US006965013B2

(12) United States Patent
Hsu

(10) Patent No.: US 6,965,013 B2
(45) Date of Patent: Nov. 15, 2005

(54) INTERMEDIN AND ITS USES

(75) Inventor: Sheau Yu Teddy Hsu, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 10/723,368

(22) Filed: Nov. 26, 2003

(65) Prior Publication Data

US 2004/0204353 A1 Oct. 14, 2004

Related U.S. Application Data

(60) Provisional application No. 60/429,327, filed on Nov. 26, 2002.

(51) Int. Cl.[7] .......................... C07K 1/00; C07K 14/00; C07K 17/00; A61K 38/00; A61K 38/04
(52) U.S. Cl. ........................ 530/350; 530/324; 530/326
(58) Field of Search ............................ 514/12; 530/350, 530/324, 326; 435/69.1, 7, 320, 325

(56) References Cited

PUBLICATIONS

Roh, J et al., NCBI direct sequence submission accession No. AF529213.*
Allen et al., Identification of Two Classes of Prolactin–Releasing Factors in Intermediate Lobe Tumors From Transgenic Mice, Endocrinology, (1995), 136:3093–3099.
Ben–Jonathan et al., Dopamine as a Proclactin (PRL) Inhibitor, Endocr. Rev., (2001), 22(6): 724–763.
Christopoulos et al., Multiple Amylin Receptors Arise From Receptor Activity–Modifying Protein Interaction With the Calcitonin Receptor Gene Product, Mol. Pharmacol., (1999), 56:235–242.
GenBank entry AF529213.

Hay et al., Knockouts and Transgenics Confirm the Importance of Adrenomedullin in the Vasculature, Trends Pharmacol. Sci., (2001), 22:57–59.
Kruger et al., Calcitonin Gene–Related Peptide (CGRP) in the Rat Central Nervous System: Patterns of Immunoreactivity and Receptor Binding Sites, Brain Res., (1988), 463:223–244.
Laudon et al., Prolactin–Releasing Factor: Cellular Origin in the Intermediate Lobe of the Pituitary, Endocrinology, (1990), 126(6):3185–3192.
McLatchie et al., Ramps Regulate the Transport and Ligand Specificity of the Calcitonin–Receptor–Like Receptor, Nature, (1998), 393:333–339.
Meeran et al., Circulating Adrenomedullin does not Regulate Systemic Blood Pressure but Increases Plasma Prolactin After Intravenous Infusion in Humans: A Pharmacokinetic Study, J. Clin. Endocrinol. Metab., (1997), 82(1):95–100.
Mulder et al., Islet Amyloid Polypeptide (Amylin)–Deficient Mice Develop a more Severe From of Alloxan–Induced Diabetes, Am. J. Physiol. Endocrinol. Metab., (2000), 278:E684–E691.

(Continued)

Primary Examiner—Jon Weber
Assistant Examiner—Robert B. Mondesi
(74) Attorney, Agent, or Firm—Pamela J. Sherwood; Bozicevic, Field & Francis LLP

(57) ABSTRACT

Intermedin nucleic acid compositions and their encoded polypeptides and variants thereof are provided. Intermedin is a novel ligand for the calcitonin receptor-like receptor. In addition to its use as a therapeutic agent, intermedin sequences are utilized in screening and research methods for the determination of specific analogs, agonists, antagonists and mimetics. Intermedin is highly expressed in the intermediate lobe of the pituitary and is shown to stimulate prolactin release by anterior pituitary cells, and to release of growth hormone. Intermedin treatment leads to blood pressure reduction both in normal and hypertensive subjects, as well as the suppression of gastric emptying activity.

4 Claims, 21 Drawing Sheets

PUBLICATIONS

Poyner et al., International Union of Pharmacology. XXXII. The Mammalian Calcitonin Gene–Related Peptides, Adrenomedullin, Amylin, and Calcitonin Receptors, Pharmacol. Rev., (2002), 54(2):233–246.

Salmon et al., Modulation of Morphine Analgesia in α CGRP Mutant Mice, Neuroreport, (1999), 10(4):849–854.

Salmon et al., Altered Neuroadaptation in Opiate Dependence and Neurogenic Inflammatory Nociception in α CGRP—Deficient Mice, Nat. Neurosci., (2001), 4:357–358.

Shindo et al., Vascular Abnormalities and Elevated Blood Pressure in Mice Lacking Adrenomedullin Gene, Circulation, (2001), 104:1964–197.

Zhang et al., Arthritic Calcitonin/α Calcitonin Gene–Related Peptide Knockout Mice have Reduced Nociceptive Hypersensitivity, Pain, (2001), 89:265–273.

* cited by examiner

A

```
atggcccggatcccgacggccgccctgggttgcatcagcctcctctgcctgcagctccctggctcgctg
 M  A  R  I  P  T  A  A  L  G  C  I  S  L  L  C  L  Q  L  P  G  S  L    23
tcccgcagcctgggcggggacccgcgacccgtcaaacccagggagccccagcccggagcccttccagc
 S  R  S  L  G  G  D  P  R  P  V  K  P  R  E  P  P  A  R  S  P  S  S    46
agcctgcagcccaggcaccccgcaccccgacctgtggtctggaagcttcaccgggccctccaggcacag
 S  L  Q  P  R  H  P  A  P  R  P  V  V  W  K  L  H  R  A  L  Q  A  Q    69
agggtgccggcctggcccctgttatgggtcagcctctccgggatggtggccgccaacactcgggcccc
 R  G  A  G  L  A  P  V  M  G  Q  P  L  R  D  G  G  R  Q  H  S  G  P    92
cgaagacactcgggcccccgcaggacccaagcccagcctgcgagtgggctgcgtgctgggcacctgc
 R  R  H  S  G  P  R  R  T  Q  A  Q  L  L  R  V  G  C  V  L  G  T  C    115
caggtgcagaatctcagccaccgcctgtggcaactcatgggaccggccggccggcaggactcagctcct
 Q  V  Q  N  L  S  H  R  L  W  Q  L  M  G  P  A  G  R  Q  D  S  A  P    138
gtggaccccagcagcccccacagctatggctga
 V  D  P  S  S  P  H  S  Y  G  *                                         148
```

B

```
              hαCGRP    ACDTATCVTHRLAGLLSRSGGVVKNNFVPTNVGSKAFG
              hβCGRP    ACNTATCVTHRLAGLLSRSGGMVKSNFVPTNVGSKAFG
              mαCGRP    SCNTATCVTHRLAGLLSRSGGVVKDNFVPTNVGSEAFG
              pαCGRP    ACNTATCVTHRLADFLSRSGGMGNSNFVPTNVGAKAFG
              pβCGRP    ACKTATCVTHRLADFLSRSGGLGYSNFVPTNVGACAFG hamylin   KCNTATCATQRLANFLVHSSNNFGAILSSTNVGSNTYG
              mamylin   KCNTATCATQRLANFLVRSSNNLGPVLPPTNVGSNTYG
              pamylin   KCNTATCVTQRLADFLVRSSNTIGTVYAPTNVGSTTYG hADM      YRQSMNNFQGLRSFGCRFGTCTVQKLAHQIYQFTDKDKDNV-APRSKISPQGYG
              mADM      YRQSMNQGSRSNGCRFGTCTFQKLAHQIYQLTDKDKDGM-APRNKISPQGYG
              pADM      SKNLVNQSRKNGCSLGTCIVHDLAFRLHQLGFQYKIDI-APVDKISPQGYG hIMD      TQAQLLRVGCVLGTCQVQNLSHRLWQLMGPAGRQDSAPVDPSSPHSYG
              mIMD      PHAQLLRVGCVLGTCQVQNLSHRLWQLVRPAGRRESAPVDPSSPHSYG
              rIMD      PHAQLLRVGCVLGTCQVQNLSHRLWQLVRPSGRRESAPVDPSSPHSYG
              pIMD1     NHVMRVACVLGTCQVQNLSHRLYQLIGQNKEDSSINPHSPHSYG
              pIMD2     RAGCALGTCQVQNLSHRLYQLIGQSGRDDSSINPKSPHSYG
              zIMD      PQLMRVGCVLGTCQVQNLSHRLYQLVGQSGRED-SEINPRSPHSYG
```

IMDL

IMDS

Fig. 1

INTERMEDIN AND ITS USES

Many aspects of physiology, including hunger, stress responses, and reproduction, are dependent on hormone balance for control. This balance can be responsive to both internal and external stimuli. For example, secretion of hormones by the anterior pituitary gland is controlled largely by the hypothalamus, a region of the brain that lies just above the gland. Hypothalamic neurons are known to make and release peptide factors that stimulate or inhibit the secretion of a particular hormone by the specific set of cells that produces it in the pituitary.

Diverse hypothalamic releasing peptides are important in the regulation of the secretion of different anterior pituitary hormones such as GH, ACTH, TSH, LH, and FSH. However, the regulation of prolactin release by the anterior pituitary is more complex, and involves stimulatory factors originating from both the hypothalamus and the intermediate lobe (see Laudon et al. (1990) *Endocrinology* 126:3185–3192; Ben-Jonathan and Hnasko (2001) *Endocr. Rev.* 22:724–763). Although the role of the intermediate lobe in the regulation of prolactin secretion is well documented, and the intermediate and posterior lobes are necessary for the suckling- and estradiol-induced rises in prolactin release, the identity of prolactin-releasing factors from the intermediate lobe remains to be characterized (Allen et al. (1995) *Endocrinology* 136:3093–3099).

The pituitary calcitonin receptor-like receptor (CRLR) has been associated with prolactin release (Meeran et al. 1997. J. Clin. Endocrinol. Metab. 82:95–100), although there is a lack of the overlapping calcitonin gene-related peptide (CGRP) expression pattern with binding sites for CGRPs in the brain (Kruger 1988. Brain Res. 463:223–244). Originally isolated as a polypeptide hormone essential for calcium balance, calcitonin belongs to a group of peptide hormones including α CGRP, β CGRP, adrenomedullin (ADM), and amylin (Eto (2001) *Peptides* 22:1693–1711). These tissue-specific peptides are important endocrine and neurocrine integrators for homeostasis maintenance in the vascular and respiratory systems.

The biological actions of these peptides are mediated via binding to two closely related type II G protein-coupled receptors (GPCRs), the calcitonin receptor and the CRLR (Christopoulos et al. (1999) *Mol. Pharmacol.* 56:235–242; Poyner et al. (2002) *Pharmacol. Rev.* 54:233–246). Although the calcitonin receptor is the main mediator for calcitonin action, it also binds amylin. Recent cloning and functional studies have shown that CGRPs, ADM, and to a lesser extent, amylin, interact with different combinations of CRLR and three receptor activity modifying proteins (RAMPs); see McLatchie et al. (1998) *Nature* 393:333–339.

Many cells express multiple RAMPs. Co-expression of the calcitonin receptor-like receptor (CRLR) and receptor activity-modifying proteins (RAMPs) is required to generate functional receptors for calcitonin gene-related peptide (CGRP) and adrenomedullin (ADM). The formation of heterodimers between RAMPs and CRLR is essential for the proper cell surface targeting and pharmacological characteristics of both CGRP and ADM receptors. The RAMP family comprises three members (RAMP1,-2, and- 3), which share less than 30% sequence identity but a common topological organization. They are small intrinsic membrane proteins (predicted sizes: $M_r$ 14,000–17,000) with a large extracellular N terminus (~100 amino acids), a single transmembrane domain, and a very short intracellular domain (10 amino acids). Co-expression of RAMP1 with CRLR leads to the formation of a CGRP receptor, whereas RAMP2 and RAMP3 promote the expression of an ADM receptor. When the calcitonin receptor is co-expressed with RAMP1 it provides for a CGRP/amylin receptor, and with RAMP3 it provides for an amylin receptor.

Studies using mutant mice deficient for α CGRP, ADM, or amylin have indicated that, in different systems, CRLR can important for cardiovascular morphogenesis, sensory neurotransmission, inflammatory reactions, nociceptive behavior, and glucose homeostasis. Thus, the physiological functions of peptides in this family are determined by receptor-binding specificity and the tissue expression profiles of individual ligands.

Peptide hormones are of great interest for clinical use and the development of therapies, including treatment of hypertension and maintenance of cardiovascular homeostasis. In addition to these effects, identification of prolcatin releasing factor is of interest. Although prolactin is important in pregnancy and lactation in mammals, and is involved in the development of the mammary glands and the promotion of milk synthesis, a specific prolactin-releasing hormone has hitherto remained unknown.

Related Publications

Hay and Smith (2001) *Trends Pharmacol. Sci.* 22:57–59; and Shindo et al, (2001) *Circulation* 104:1964–197 discuss the importance of adrenomedullin in the vasculature. The role of a CGRP is discussed by Zhang et al. (2001) *Pain* 89:265–273; Salmon et al, (1999) *Neuroreport* 10:849–854; and Salmon et al. (2001) *Nat. Neurosci.* 4:357–358. The role of amylin is discussed by Mulder et al. (2000) *Am. J. Physiol. Endocrinol. Metab.* 278:E684–691.

GenBank entry AF529213.

SUMMARY OF THE INVENTION

Intermedin nucleic acid compositions and their encoded polypeptides and variants thereof are provided. Intermedin is a novel ligand for the calcitonin receptor-like receptor. In addition to its use as a therapeutic agent, intermedin sequences are utilized in screening and research methods for the determination of specific analogs, agonists, antagonists and mimetics.

Intermedin is highly expressed in the intermediate lobe of the pituitary and is shown to stimulate prolactin release by anterior pituitary cells. Intermedin binds to CGRP/ adrenomedullin receptors with high affinity and increases cAMP production in cells expressing the calcitonin receptor-like receptor (CRLR). Intermedin treatment leads to blood pressure reduction both in normal and hypertensive subjects, as well as the suppression of gastric emptying activity. Intermedin finds use as a hypotensive agent, as a cardioprotective agent, in the regulation of gastrointestinal motility, and in stimulating the release of prolactin, e.g. as an aid in fertilization, lactation, pre-term labor, and the like. Intermedin also regulated the release of growth hormone, and is involved in the regulation of body growth.

The invention also provides diagnostics and therapeutics comprising intermedin encoding nucleic acids, the corresponding genes and gene products, antisense nucleotides, and antibodies specific for one or more epitopes of the intermedin polypeptide. The nucleic acid compositions find use in identifying homologous or related genes; for production of the encoded peptide; in producing compositions that modulate the expression or function of its encoded protein; for gene therapy; mapping functional regions of the protein; and in studying associated physiological pathways. In addition, modulation of the gene activity in vivo is used for prophylactic and therapeutic purposes.

BRIEF DESCRIPTION OF THE DRAWINGS

FIGS. 1A–1C. Cloning of intermedin and elucidation of its identity. (a) The human intermedin gene encodes a 148-amino-acid ORF with a 24-amino-acid signal peptide for secretion at the N-terminus and a mature amidated peptide of 47 amino acids. The sequence identity of human intermedin was first deduced from EST and genomic sequences, followed by subcloning using gene-specific primers. Amino acid numbers are on the right and the stop codon is marked with an asterisk. The putative mature peptide is underlined whereas the N-terminal signal peptide for secretion is lightly shaded. The ATG start site and the putative C-terminal amidation donor residue are in bold letters. The putative basic cleavage sites are highlighted by a dark background. (b) Comparison of CGRP-related peptides (α CGRP, β CGRP, amylin, ADM, and intermedin (IMD)) from mammals and fish. Sequence alignment of these genes from human indicated the sequence homology between intermedin and paralogous peptides is restricted to the mature peptide and no similarity was found in the putative preproregion. The two intermedins from puffer fish (*Takifugu rubripes*) are indicated as IMD1 and IMD2, respectively. The putative secondary structures of mature CGRP peptides are indicated above the alignment whereas the putative secondary structures of mature intermedins are shown below the alignment, as random coil, curved line; extended strand, round cylinder; helix, wavy banner. The two cysteines and one neighboring threonine residue shared by all aligned peptides are enclosed by lines. Residues shared by ADM and intermedin from different vertebrates are indicated by bold asterisks between the ADM and intermedin alignment. In the alignment, residues shared by highly conserved orthologous sequences of each gene are lightly shaded. h:human; m:mouse; r:rat; p:puffer fish; z:zebrafish. (c) The phylogenetic relationship among twelve representative CGRP related peptides. h:human; m:mouse; p:puffer fish.

Intermedin-long (IMDL), intermedin-short (IMDS), and ADM dose-dependently suppressed systolic blood pressure in male Sprague-Dawley rats. Blood pressure change was monitored for 40 min, and averages at 10, 20, and 30 min were presented. B Increase in heart rate from treatment with different doses of IMDL, IMDS, or ADM in male Sprague-Dawley rats. C. Blockage of the hypotensive effect of intermedin by the CGRP receptor antagonist, CGRP8–37, and the putative intermedin receptor-binding domain peptide, IMD17–47. D. Suppression of blood pressure in male spontaneously hypertensive rats (SHR) by intermedin and the blockage of intermedin effects by receptor antagonists.

Figure 7:
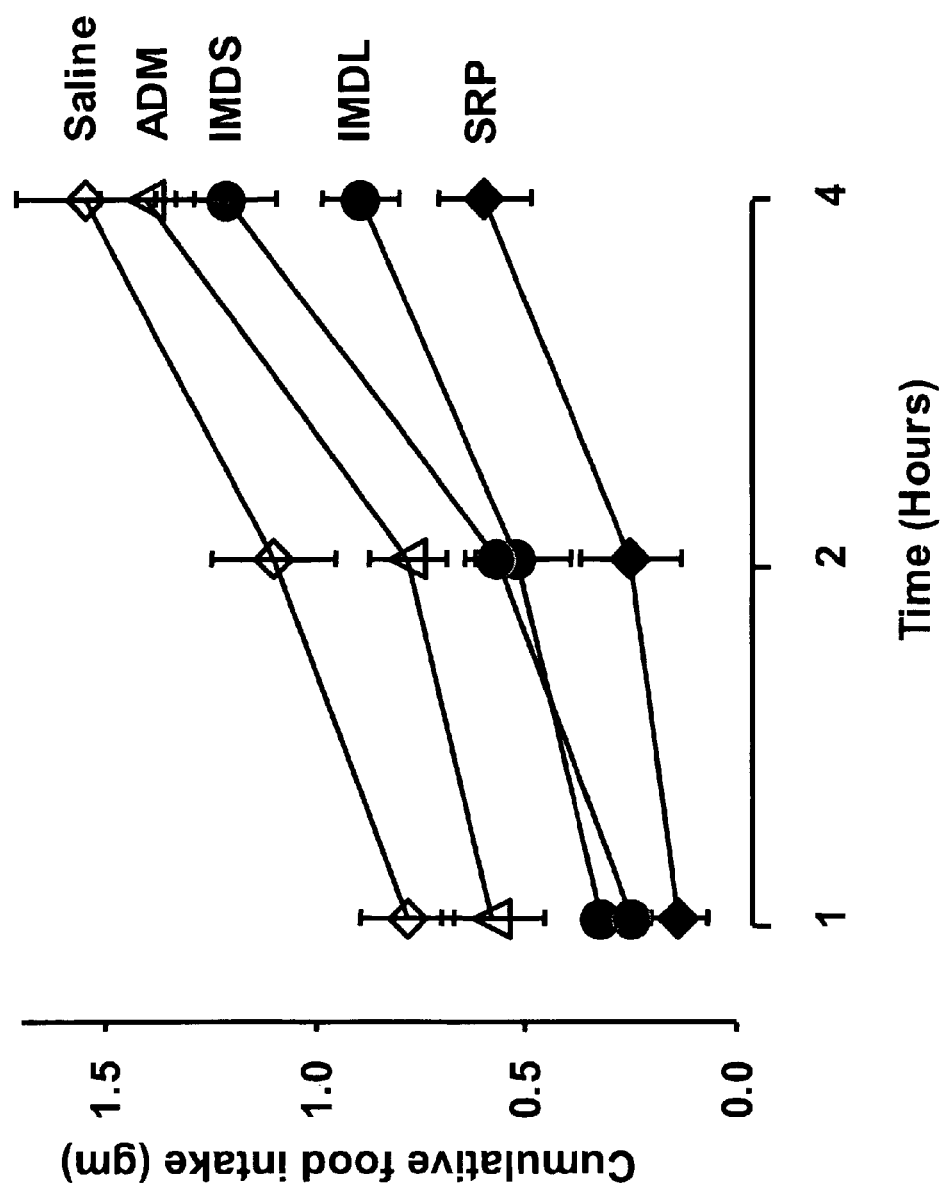

FIG. 7. Suppression of food intake by intermedin in fasted mice. Cumulative food intake in mice treated with saline (PBS, N=29), intermedin-long (IMDL, 100 nM/Kg, N=17), intermedin-short (IMDS, 100 nM/Kg, N=16), ADM (100 nM/Kg, N=20), or a type II CRH receptor-selective agonist SRP/urocortin II (15,23)(SRP, 100 nM/Kg, N=10) at 1, 2, and 4 h after treatment. *, significantly different from control animals injected with saline alone (P<0.05).

Figure 8:
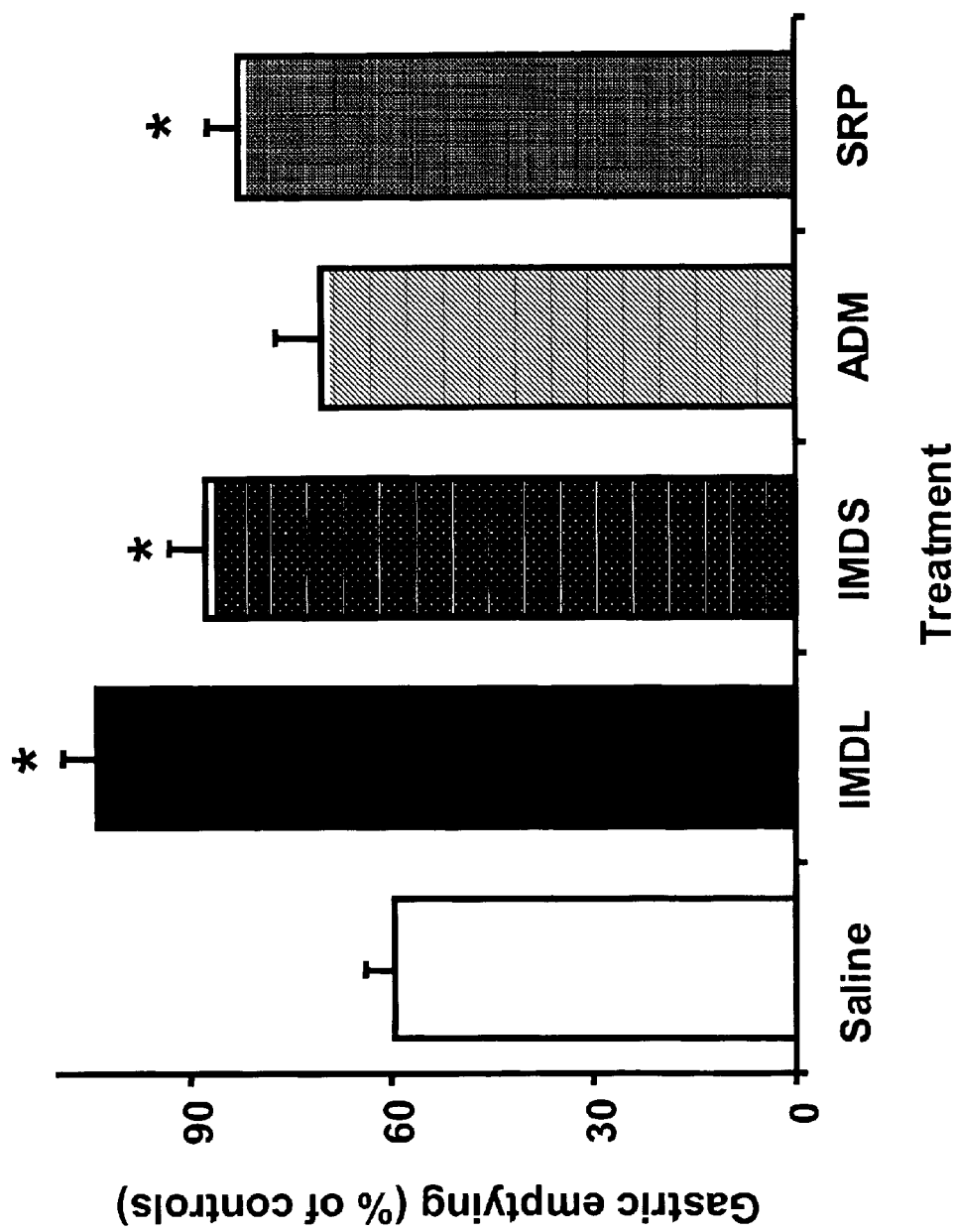

FIG. 8. Suppression of gastric emptying activity by intermedin. Reduction of gastric emptying by intermedin-long (IMDL, 100 nM/Kg, N=24), intermedin-short (IMDS, 100 nM/Kg, N=20), ADM (100 nM/Kg, N=27), and SRP/urocortin II (100 nM/Kg, N=10) at 90 min after hormone treatment as compared to control animals receiving saline injection (N=31). Gastric emptying was calculated by comparing the stomach weight of treated mice to the stomach weight of control mice receiving no hormone treatment and killed at the time of hormone injection. Additional animals injected with saline and sacrificed at the same time as hormone-treated animals were used as experimental controls. *, significantly different from control animals injected with saline alone (P<0.05).

DESCRIPTION OF THE SPECIFIC EMBODIMENTS

The invention provides novel nucleic acid and polypeptide compositions, referred to herein as intermedins, which are members of the calcitonin peptide hormone family. Intermedin is a novel ligand for the calcitonin receptor-like receptor. In addition to its use as a therapeutic agent, intermedin sequences are utilized in screening and research methods for the determination of specific analogs, agonists, antagonists and mimetics.

The human intermedin gene encodes a 148-amino-acid open reading frame, with a 24-amino-acid signal peptide for secretion at the N-terminus and a mature amidated peptide (shown in SEQ ID NO:1 and SEQ ID NO:2, and in FIG. 1A).

In one embodiment of the invention, the mature intermedin peptide is a 40-amino-acid peptide (intermedin-short or IMDS), set forth as SEQ ID NO:5, residues 8–47. In another embodiment of the invention, the mature intermedin peptide is a 47-amino-acid mature peptide (intermedin-long or IMDL), set forth as SEQ ID NO:5, 1–47. The amidated form of these intermedin peptides is a specific ligand for the calcitonin receptor like receptor. Intermedin is expressed in the intermediate lob of the pituitary, as well as in other tissues, e.g. gastrointestinal tissues.

The nucleic acid compositions of the subject invention find use in identifying homologous or related genes; for production of the encoded protein; in producing compositions that modulate the expression or function of its encoded protein; for gene therapy; mapping functional regions of the protein; and in studying associated physiological pathways. In addition, modulation of the gene activity in vivo is used for prophylactic and therapeutic purposes. The proteins are useful as a therapeutic, as an immunogen for producing specific antibodies, in screening for biologically active agents that act in the prlactin and CRLR signaling pathways and for therapeutic and prophylactic purposes.

Intermedins are ligands of the CRLR receptor, and are shown to activate the receptor upon binding. Activation by intermedin results in the release of prolactin, regulation of growth hormone release, in vascular system effects including lowering of blood pressure and vasodilation, and in gastrointestimal effects. Thus, intermedin signals through the CRLR to stimulate prolactin release from the anterior pituitary, regulation of growth hormone release, and to regulate peripheral vasodilatation-related processes. Intermedin can act on different peripheral tissues and provides a new therapeutic agent for pathologies associated with vascular and gastrointestinal disorders.

INTERMEDIN POLYPEPTIDES

The mature intermedin polypeptide is a 47 amino acid peptide, derived from a 148 amino acid precursor protein (SEQ ID NO:5). The amino acid sequence of the precursor protein and mature protein are provided in SEQ ID NO:2. The nucleotide sequence of human intermedin cDNA is provided as SEQ ID NO:1. The human intermedin ORF contains a signal peptide for secretion (shown in SEQ ID NO:2) and the predicted mature region is preceded by a potential diarginine proteolytic cleavage sites, and an C-terminal α-amidation donor residue.

For use in the subject methods, native intermedin or modifications thereof may be used. Peptides of interest as immunogens and for screening methods, e.g. competitive receptor binding, include fragments of at least about 12 contiguous amino acids, more usually at least about 20 contiguous amino acids, and may comprise 30 or more amino acids, up to the provided peptide, and may extend further to comprise other sequences present in the precursor protein. Peptides of interest for therapeutic purposes may include all or substantially all of the provided peptide, or may comprise fragments thereof that retain the biological activity of intermedin. Generally such peptides are amidated, and may comprise substantially all of the mature peptide sequence, i.e. at least about 20 contiguous amino acid resides, at least about 30 contiguous amino acid resides, and may comprise 45 contiguous amino acids residues, or more. Deletions may extend from residue 1 through 10 of the peptide, and may further delete additionally amino acids at residues 10–15 or more. Smaller deletions, of from 1 to to 5 amino acids, may be deleted in the N-terminus.

The sequence of the intermedin polypeptide may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) *J. Biol. Chem.* 275:23783–23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

USES OF INTERMEDIN

In light of the pharmacologic activities of intermedin, numerous clinical indications are evident. For example, clinical indications for which a intermedin peptide or variants thereof may find use include treatment of hypertension, as a cardioprotective agent, as a diet aid, and for the relase of prolactin, which has effects on the uterus and pregnancy, e.g. in the regulation of preterm labor, blood pressure regulation during pregnancy, etc.; in growth hormone release from the pituitary; and in ovarian follicle survival and growth, e.g. for the culture of follicles for use in in vitro fertilization.

Hypertension is a disease which, if untreated, strongly predisposes to atherosclerotic cardiovascular disease. It is estimated that as many as 1 in 4 adult Americans have hypertension. Hypertension is approximately twice as common in persons with diabetes as in those without. The prevalence of hypertension increases with age.

Hypertension should not be diagnosed on the basis of a single measurement. Initial elevated readings should be confirmed on at least two subsequent visits over one week or more with average diastolic blood pressure of 90 mmHg or greater or systolic blood pressure of 140 mmHg or greater required for diagnosis of hypertension. Special care is warranted in diagnosing hypertension in persons with diabetes because of greater variability of blood pressure and a much greater likelihood of isolated systolic hypertension. A goal blood pressure of less than 130/85 mmHg is recommended for these patients.

In addition to dietary changes, pharmacological treatment may be required to control high blood pressure. The subject peptides may be administered to reduce arterial blood pressure. In addition, a secondary effect of reducing hypertension is reduction of edema and inflammatory exudate volume.

Pharmaceutical compositions containing intermedin peptides and derivatives therefrom are useful as cardioprotective agents, e.g. to ameliorate ischemic injury or myocardial infarct size consequent to myocardial ischemia. The development of new therapeutic agents capable of limiting the extent of myocardial injury, i.e., the extent of myocardial infarction, following acute myocardial ischemia is a major concern of modern cardiology. There has also been interest in the development of therapies capable of providing additional myocardial protection which could be administered in conjunction with thrombolytic therapy, or alone, since retrospective epidemiological studies have shown that mortality during the first few years following infarction appears to be related to original infarct size.

Myocardial ischemia is the result of an imbalance of myocardial oxygen supply and demand and includes exertional and vasospastic myocardial dysfunction. Exertional ischemia is generally ascribed to the presence of critical atherosclerotic stenosis involving large coronary arteries resulting in a reduction in subendocardial flow. Vasospastic ischemia is associated with a spasm of focal variety, whose onset is not associated with exertion or stress. The spasm is better defined as an abrupt increase in vascular tone.

The compounds of this invention can be normally administered orally or parenterally, in the treatment of patients in need of cardioprotective therapy. The dosage regimen is that which insures maximum therapeutic response until improvement is obtained and thereafter the minimum effective level that gives relief. Thus, in general, the dosages are those that are therapeutically effective in producing a cardioprotective effect, i.e., amelioration of ischemic injury or myocardial infarct size consequent to myocardial ischemia. It is also anticipated that the peptides would be useful as an injectable dosage form which may be administered in an emergency to a patient suffering from myocardial ischemia, etc.

The intermedin peptides and derivatives therefrom also find use in the reduction of edema, for example in rheumatoid arthritis, edema secondary to brain tumors or irradiation for cancer, edema resulting from stroke, head trauma or spinal cord injury, post-surgical edema, asthma and other respiratory diseases and cystoid macular edema of the eye.

Administration of intermedin results in a release of prolactin, and regulation of growth hormone release. Prolactin is a polypeptide hormone that is synthesized in and secreted from specialized cells of the anterior pituitary gland, the lactotrophs. Prolactin serves multiple roles in reproduction, but it also plays multiple homeostatic roles in the organism. Synthesis and secretion of prolactin is not restricted to the anterior pituitary gland, but other organs and tissues in the body have this capability.

Based on its genetic, structural, binding and functional properties, prolactin belongs to the prolactin/growth hormone/placental lactogen family group I of the helix bundle protein hormones. The prolactin molecule is arranged in a single chain of amino acids with three intramolecular disulfide bonds between six cysteine residues. In humans it consists of 199 amino acids with a molecular mass of ~23,000 Da. The prolactin-R is a single membrane-bound protein that belongs to class 1 of the cytokine receptor superfamily. The signal transducer and activator of transcription (STAT) protein family has been shown to be a major transducer in cytokine receptor signaling. STAT1, STAT3, and especially STAT5a and STAT5b, have been identified as transducer molecules of the prolactin-R.

The varied effects of prolactin on the mammary gland include growth and development of the mammary gland, synthesis of milk, and maintenance of milk secretion. Lactogenesis clearly requires pituitary prolactin, since hypophysectomy during pregnancy prevents subsequent lactation.

Actions of prolactin on luteal function depend on species and the stage of the estrous cycle. Prolactin acts as a luteotrophic hormone by maintaining the structural and functional integrity of the corpus luteum. This "luteotrophic" action of prolactin is characterized by enhanced progesterone secretion. Prolactin enhances progesterone secretion two ways: prolactin potentiates the steroidogenic effects of luteinizing hormone (LH) in granulosa-luteal cells and inhibits the 20α-hydroxysteroid dehydrogenase enzyme, which inactivates progesterone. In humans, high levels of prolactin inhibit granulosa cell luteinization and steroidogenesis. Prolactin is essential for progesterone biosynthesis and luteal cell hypertrophy during pregnancy. In addition to luteal function, the prolactin-R mediates numerous functions in granulosa cells and oocytes as well.

Aside from its actions on reproductive processes, prolactin plays a role in maintaining the constancy of the internal environment by regulation of the immune system, osmotic balance, and angiogenesis. Prolactin is a common mediator of the immunoneuroendocrine network, where nervous, endocrine, and immune systems communicate with each other. Its main feature is cooperation with cytokines and hemopoietins, and it has been implicated as a 'stress hormone', functioning to restore hematopoietic homeostasis under conditions of dysregulation. Prolactin plays a significant role in regulation of the humoral and cellular immune responses in physiological as well as pathological states, such as autoimmune diseases. Immune responses in vivo are enhanced by prolactin, including T cell proliferation and mitogenesis; maturation of dendritic cells, etc. Circulating prolactin is elevated in a number of autoimmune diseases, and about 20% of SLE patients are hyperprolactinemic.

Prolactin also regulates solute and water transport across mammalian cell membranes. For example, prolactin exerts a host of activities on transport of solute across mammary epithelial cell membranes. Prolactin decreases the transport of sodium and increases the transport of potassium across mammary epithelial cells. Prolactin also affects water transport across amniotic membranes. Prolactin is responsible for fluid, sodium, chloride, and calcium transport across intestinal epithelial membranes.

Angiogenesis, the development of blood vessels, is inhibited by proteolytic fragments of native prolactin. This anti-angiogenic activity is inherent to the 16-kDa fragment. In contrast, intact human prolactin has angiogenic activities.

COMPOUND SCREENING

The availability of purified intermedin and other components in the signaling pathways, e.g. RAMP1, RAMP2, RAMP3, CRLR, prolactin, prolactin receptor, STAT proteins etc., allows in vitro reconstruction of the pathway. Two or more of the components may be combined in vitro, and the behavior assessed in terms of activation of transcription of specific target sequences; modification of protein components, e.g. proteolytic processing, phosphorylation, methylation, etc.; ability of different protein components to bind to each other, etc. The components may be modified by sequence deletion, substitution, etc. to determine the functional role of specific residues.

Drug screening may be performed using an in vitro model, a genetically altered cell or animal, or purified intermedin protein. One can identify ligands or substrates that compete with, modulate or mimic the action of intermedin. Areas of investigation include the development of treatments as a cardioprotective agent; for treatment of hypertension; for activity relating to the release of prolactin, regulation of growth hormone release; etc.

Drug screening identifies agents that mimic intermedin activity, either as an antagonist or as an agonist. A wide variety of assays may be used for this purpose, including labeled in vitro protein-protein binding assays, electrophoretic mobility shift assays, immunoassays for protein binding, and the like. Knowledge of the 3-dimensional structure of intermedin, derived from crystallization of purified synthetic intermedin protein, leads to the rational design of small drugs that specifically inhibit intermedin activity.

The term "agent" as used herein describes any molecule, e.g. protein or pharmaceutical, with the capability of altering or mimicking the physiological function of intermedin. Generally, a plurality of assay mixtures are run in parallel with different agent concentrations to obtain a differential response to the various concentrations. Typically one of these concentrations serves as a negative control, i.e., at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of hypertension, etc. The compounds may also be used to enhance intermedin function as a cardioprotective agent; for treatment of hypertension; for appetite suppression, for activity relating to the release of prolactin, regulation of growth hormone release; etc. The agents may be administered in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1–10 wt %.

ANTIBODIES SPECIFIC FOR INTERMEDIN POLYPEPTIDES

The present invention provides antibodies specific for intermedin polypeptides, e.g. any one of the variants, polypeptides, or domains described above. Such antibodies are useful, for example, in methods of detecting the presence of intermedin in a biological sample, and in methods of isolating intermedin from a biological sample.

The intermedin polypeptides of the invention are useful for the production of antibodies, where short fragments provide for antibodies specific for the particular polypeptide, and larger fragments or the entire protein allow for the production of antibodies over the surface of the polypeptide. As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme that generates a detectable product, a green fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

"Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for a intermedin polypeptide, particularly a human intermedin polypeptide.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. Coli*, and the heavy and light chains mixed to further enhance the affinity of the antibody. Alternatives to in vivo immunization as a method of raising antibodies include binding to phage display libraries, usually in conjunction with in vitro affinity maturation.

FORMULATIONS

The compounds of this invention can be incorporated into a variety of formulations for therapeutic administration. Particularly, agents that modulate intermedin activity, or intermedin polypeptides and analogs thereof are formulated for administration to patients for the treatment of intermedin dysfunction, where the intermedin activity is undesirably high or low. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The intermedin may be systemic after administration or may be localized by the use of an implant that acts to retain the active dose at the site of implantation.

In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the site of infection, so that the local concentration of active agent is increased relative to the rest of the body.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 µg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

Liposomes may be used for gene or protein delivery in vivo and in vitro. The liposomes employed in the present invention can be prepared using any one of a variety of conventional liposome preparatory techniques. As will be readily apparent to those skilled in the art, such conventional techniques include sonication, chelate dialysis, homogenization, solvent infusion coupled with extrusion, freeze-thaw extrusion, microemulsification, as well as others. These techniques, as well as others, are discussed, for example, in U.S. Pat. No. 4,728,578, U.K. Patent Application G.B. 2193095 A, U.S. Pat. No. 4,728,575, U.S. Pat. No. 4,737,323, International Application PCT/US85/01161, Mayer et al., Biochimica et Biophysica Acta, Vol. 858, pp. 161–168 (1986), Hope et al., Biochimica et Biophysica Acta, Vol. 812, pp. 55–65 (1985), U.S. Pat. No. 4,533,254, Mahew et al., Methods In Enzymology, Vol. 149, pp. 64–77 (1987), Mahew et al., Biochimica et Biophysica Acta, Vol. 75, pp. 169–174 (1984), and Cheng et al., Investigative Radiology, Vol. 22, pp. 47–55 (1987). A solvent free system similar to that described in International Application PCT/US85/01161 may be employed in preparing the liposome constructions.

The materials that are utilized in preparing the liposomes include any of the materials or combinations thereof known to those skilled in the art as suitable in liposome construction. The lipids used may be of either natural or synthetic origin. Such materials include, but are not limited to, lipids such as cholesterol, phosphatidylcholine, phosphatidylethanolamine, phosphatidylserine, phosphatidylglycerol, phosphatidic acid, phosphatidylinositol, lysolipids, fatty acids, sphingomyelin, glycosphingolipids, glucolipids, glycolipids, sulphatides, lipids with amide, ether, and ester-linked fatty acids, polymerizable lipids, and combinations thereof. As one skilled in the art will recognize, the liposomes may be synthesized in the absence or presence of incorporated glycolipid, complex carbohydrate, protein or synthetic polymer, using conventional procedures. The surface of a liposome may also be modified with a polymer, such as, for example, with polyethylene glycol (PEG), using procedures readily apparent to those skilled in the art. Any species of lipid may be used, with the sole proviso that the lipid or combination of lipids and associated materials incorporated within the lipid matrix should form a bilayer phase under physiologically relevant conditions. As one skilled in the art will recognize, the composition of the liposomes may be altered to modulate the biodistribution and clearance properties of the resulting liposomes.

The membrane bilayers in these structures typically encapsulate an aqueous volume, and form a permeability barrier between the encapsulated volume and the exterior solution. Lipids dispersed in aqueous solution spontaneously form bilayers with the hydrocarbon tails directed inward and the polar headgroups outward to interact with water. Simple agitation of the mixture usually produces multilamellar vesicles (MLVs), structures with many bilayers in an onion-like form having diameters of 1–10.mu.m (1000–10,000 nm). Sonication of these structures, or other methods known in the art, leads to formation of unilamellar vesicles (UVs) having an average diameter of about 30–300 nm. However, the range of 50 to 200 nm is considered to be optimal from the standpoint of, e.g., maximal circulation time in vivo. The actual equilibrium diameter is largely determined by the nature of the phospholipid used and the extent of incorporation of other lipids such as cholesterol. Standard methods for the formation of liposomes are known in the art, for example, methods for the commercial production of liposomes are described in U.S. Pat. No. 4,753,788, and U.S. Pat. No. 4,935,171.

Polymerized liposomes are self-assembled aggregates of lipid molecules, and are described in U.S. Pat. Nos. 5,512,294, 6,132,764, and U.S. Pat. Application 20020071843. The hydrophobic tail groups of polymerizable lipids are derivatized with polymerizable groups, such as diacetylene groups, which irreversibly cross-link, or polymerize, when exposed to ultraviolet light or other radical, anionic or cationic, initiating species, while maintaining the distribution of functional groups at the surface of the liposome. The resulting polymerized liposome particle is stabilized against fusion with cell membranes or other liposomes and stabilized towards enzymatic degradation. The size of the polymerized liposomes can be controlled by extrusion or other methods known to those skilled in the art. Polymerized liposomes may be comprised of polymerizable lipids, but may also comprise saturated and non-alkyne, unsaturated lipids. The polymerized liposomes can be a mixture of lipids, which provide different functional groups on the hydrophilic exposed surface. For example, some hydrophilic head groups can have functional surface groups, for example, biotin, amines, cyano, carboxylic acids, isothiocyanates, thiols, disulfides, α-halocarbonyl compounds, α, β-unsaturated carbonyl compounds and alkyl hydrazines. These groups can be used for attachment of nucleic acid sequences.

Molecules such as peptides, DNA or RNA may be attached to the outside of the liposome for gene therapy applications. The liposome structure can be readily injected and form the basis for both sustained release and drug delivery to specific cell types, or parts of the body.

For use in the above described formulations, intermedin or derivatives therefrom may be synthesized and stored as a solid lyophilized powder which is reconstituted into a pharmaceutically acceptable liquid immediately prior to use. Such formulations are usually preferred because it is recognized by those skilled in the art that lyophilized preparations generally maintain pharmaceutical activity better over time than their liquid counterparts.

In addition, intermedins and their analogs could be applied topically on the skin as well as administered as aerosal sprays.

Alternatively, the peptides may be formulated as a liquid, e.g. comprising a buffer at a concentration of from about 1 mM to about 50 mM that functions to maintain the pH, wherein the anion of said buffer may be selected from the group consisting of acetate, phosphate, carbonate, succinate, citrate, borate, tartrate, fumarate and lactate; and an alcohol which may be selected from the group consisting of mannitol, sorbitol, ribotol, arabitol, xylitol, inositol, galactitol, methanol, ethanol and glycerol. Other additives may include amino acids such as methionine, arginine, lysine, glutamic acid, cysteine, glutathione, and the like, where amino acids are generally present in concentrations ranging from about 1 mM to about 100 mM. Various sugars are optionally included in the formulations, including, for example, glucose, sucrose, lactose, fructose, trehalose, mannose, and the like. Additive sugars are generally present in concentrations ranging from about 1% to about 10%.

INTERMEDIN NUCLEIC ACIDS

The invention includes nucleic acids having a sequence set forth in SEQ ID NO:1; nucleic acids that hybridize under stringent conditions, particularly conditions of high stringency, to the sequences set forth in SEQ ID NO:1; genes corresponding to the provided nucleic acids; sequences encoding intermedins; and fragments and derivatives thereof. Other nucleic acid compositions contemplated by and within the scope of the present invention will be readily apparent to one of ordinary skill in the art when provided with the disclosure here.

The nucleic acids of the invention include nucleic acids having sequence similarity or sequence identity to SEQ ID NO:1. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided nucleic acid sequence, e.g. allelic variants, genetically altered versions of the gene, etc., bind to SEQ ID NO:1 and FIG. 1 under stringent hybridization conditions. By using probes, particularly labeled probes of DNA sequences, one can isolate homologous or related genes. The source of homologous genes can be any species, e.g. primate species, particularly human; rodents, such as rats and mice; canines, felines, bovines, ovines, equines, fish, yeast, nematodes, etc.

In one embodiment, hybridization is performed using at least 18 contiguous nucleotides (nt) of SEQ ID NO:1, or a DNA encoding the polypeptide of SEQ ID NO:2. Such a probe will preferentially hybridize with a nucleic acid comprising the complementary sequence, allowing the identification and retrieval of the nucleic acids that uniquely hybridize to the selected probe. Probes of more than 18 nt can be used, e.g., probes of from about 18 nt to about 25, 50, 100, 250, or 500 nt, but 18 nt usually represents sufficient sequence for unique identification.

Nucleic acids of the invention also include naturally occurring variants of the nucleotide sequences (e.g., degenerate variants, allelic variants, etc.). Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25–30% base pair (bp) mismatches relative to the selected nucleic acid probe. In general, allelic variants contain 15–25% bp mismatches, and can contain as little as even 5–15%, or 2–5%, or 1–2% bp mismatches, as well as a single bp mismatch.

The invention also encompasses homologs corresponding to the nucleic acids of SEQ ID NO:1, or a DNA encoding the polypeptide of SEQ ID NO:2, where the source of homologous genes can be any mammalian species, e.g., primate species, particularly human; rodents, such as rats; canines, felines, bovines, ovines, equines, fish, yeast, nematodes, etc. Between mammalian species, e.g., human and mouse, homologs generally have substantial sequence similarity, e.g., at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared. Algorithms for sequence analysis are known in the art, such as gapped BLAST, described in Altschul et al. *Nucl. Acids Res.* (1997) 25:3389–3402.

The subject nucleic acids can be cDNAs or genomic DNAs, as well as fragments thereof, particularly fragments that encode a biologically active polypeptide and/or are useful in the methods disclosed herein (e.g., in diagnosis, as a unique identifier of a differentially expressed gene of interest, etc.). The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' and 3' end of the transcribed region. The genomic DNA can be isolated as a fragment of 100 kbp or smaller; and substantially free of flanking chromosomal sequence. The genomic DNA flanking the coding region, either 3' and 5', or internal regulatory sequences as sometimes found in introns, contains sequences required for proper tissue, stage-specific, or disease-state specific expression.

The nucleic acid compositions of the subject invention can encode all or a part of the subject polypeptides. Double or single stranded fragments can be obtained from the DNA sequence by chemically synthesizing oligonucleotides in accordance with conventional methods, by restriction enzyme digestion, by PCR amplification, etc. Isolated nucleic acids and nucleic acid fragments of the invention comprise at least about 18, about 50, about 100, to about 500 contiguous nt selected from the nucleic acid sequence as shown in SEQ ID NO:1. For the most part, fragments will be of at least 18 nt, usually at least 25 nt, and up to at least about 50 contiguous nt in length or more.

Probes specific to the nucleic acid of the invention can be generated using the nucleic acid sequence disclosed in SEQ ID NO:1, or a DNA encoding the polypeptide of SEQ ID NO:2. The probes are preferably at least about 18 nt, 25 nt or more of the corresponding contiguous sequence. The probes can be synthesized chemically or can be generated from longer nucleic acids using restriction enzymes. The probes can be labeled, for example, with a radioactive, biotinylated, or fluorescent tag. Preferably, probes are designed based upon an identifying sequence of one of the provided sequences. More preferably, probes are designed based on a contiguous sequence of one of the subject nucleic acids that remain unmasked following application of a masking program for masking low complexity (e.g., BLASTX) to the sequence, i.e., one would select an unmasked region, as indicated by the nucleic acids outside the poly-n stretches of the masked sequence produced by the masking program.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

MODULATION OF INTERMEDIN EXPRESSION

The intermedin genes, gene fragments, or the encoded protein or protein fragments are useful in gene therapy to treat disorders associated with intermedin defects. Inhibition or upregulation of expression is achieved in a number of ways. Coding sequences may be introduced to increase expression levels. Antisense intermedin sequences may be administered to inhibit expression. Competitive binding antagonists, for example, a peptide that mimics intermedin binding may be used to inhibit activity. Other inhibitors are identified by screening for biological activity in an intermedin-based binding assay.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; encode a dominant negative mutation, or dominant or constitutively active mutations of native sequences; altered regulatory sequences, etc.

Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination.

Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

A variety of host-expression vector systems may be utilized to express a genetic coding sequence. Expression constructs may contain promoters derived from the genome of mammalian cells, e.g., metallothionein promoter, elongation factor promoter, actin promoter, etc., from mammalian viruses, e.g., the adenovirus late promoter; the vaccinia virus 7.5K promoter, SV40 late promoter, cytomegalovirus, etc.

In mammalian host cells, a number of viral-based expression systems may be utilized, e.g. retrovirus, lentivirus, adenovirus, herpesvirus, and the like. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts (see Logan & Shenk, 1984, Proc. Natl. Acad. Sci. USA 81:3655–3659). Specific initiation signals may also be required for efficient translation of inserted gene product coding sequences. These signals include the ATG initiation codon and adjacent sequences. Standard systems for generating adenoviral vectors for expression on inserted sequences are available from commercial sources, for example the Adeno-XT™ expression system from Clontech (Clontechniques (January 2000) p. 10–12).

In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al, 1987, Methods in Enzymol. 153:516–544).

In a preferred embodiment, methods are used that achieve a high efficiency of transfection, and therefore circumvent the need for using selectable markers. These may include adenovirus infection (see, for example Wrighton, 1996, J. Exp. Med. 183: 1013; Soares, J. Immunol., 1998, 161: 4572; Spiecker, 2000, J. Immunol 164: 3316; and Weber, 1999, Blood 93: 3685); and lentivirus infection (for example, International Patent Application WO000600; or WO9851810). Adenovirus-mediated gene transduction of endothelial cells has been reported with 100% efficiency. Retroviral vectors also can have a high efficiency of infection with endothelial cells, provides virtually 100% report a 40–77% efficiency. Other vectors of interest include lentiviral vectors, for examples, see Barry et al. (2000) *Hum Gene Ther* 11(2):323–32; and Wang et al. (2000) *Gene Ther* 7(3):196–200.

Viral vectors include retroviral vectors (e.g. derived from MOMLV, MSCV, SFFV, MPSV, SNV etc), lentiviral vectors (e.g. derived from HIV-1, HIV-2, SIV, BIV, FIV etc.), adeno-associated virus (MV) vectors, adenoviral vectors (e.g. derived from Ad5 virus), SV40-based vectors, Herpes Simplex Virus (HSV)-based vectors etc. A vector construct may include drug resistance genes (neo, dhfr, hprt, gpt, bleo, puro etc) enzymes (β-galactosidase, alkaline phosphatase etc) fluorescent genes (e.g. GFP, RFP, BFP, YFP) or surface markers (e.g. CD24, NGFr, Lyt-2 etc).

In one embodiment, the genetic agent is an antisense sequence that acts to reduce expression of the complementary sequence. Antisense nucleic acids are designed to specifically bind to RNA, resulting in the formation of RNA-DNA or RNA-RNA hybrids, with an arrest of DNA replication, reverse transcription or messenger RNA translation. Antisense molecules inhibit gene expression through various mechanisms, e.g. by reducing the amount of mRNA available for translation, through activation of RNAse H, or steric hindrance. Antisense nucleic acids based on a selected nucleic acid sequence can interfere with expression of the corresponding gene. Antisense nucleic acids can be generated within the cell by transcription from antisense constructs that contain the antisense strand as the transcribed strand.

The anti-sense reagent can also be antisense oligonucleotides (ODN), particularly synthetic ODN having chemical modifications from native nucleic acids, or nucleic acid constructs that express such anti-sense molecules as RNA. One or a combination of antisense molecules may be administered, where a combination may comprise multiple different sequences. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like.

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene. A combination of sequences may also be used, where several regions of the mRNA sequence are selected for antisense complementation.

Antisense oligonucleotides can be chemically synthesized by methods known in the art. Preferred oligonucleotides are chemically modified from the native phosphodiester structure, in order to increase their intracellular stability and binding affinity. A number of such modifications have been described in the literature that alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity, e.g. morpholino oligonucleotide analogs. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

As an alternative method, dominant negative mutations are readily generated for corresponding proteins. These may act by several different mechanisms, including mutations in a substrate-binding domain; mutations in a catalytic domain; mutations in a protein binding domain (e.g. multimer forming, effector, or activating protein binding domains); mutations in cellular localization domain, etc. See Rodriguez-Frade et al. (1999) *P.N.A.S.* 96:3628–3633; suggesting that a specific mutation in the DRY sequence of chemokine receptors can produce a dominant negative G protein linked receptor; and Mochly-Rosen (1995) *Science* 268:247.

DIAGNOSTIC USES

DNA-based reagents derived from the sequence of intermedin, e.g. PCR primers, oligonucleotide or cDNA probes, as well as antibodies against intermedin, are used to screen patient samples, e.g. biopsy-derived tissues, blood samples, etc., for amplified intermedin DNA, or increased expression of intermedin mRNA or proteins. DNA-based reagents are also designed for evaluation of chromosomal loci implicated in certain diseases e.g. for use in loss-of-heterozygosity (LOH) studies, or design of primers based on intermedin coding sequence.

The polynucleotides of the invention can be used to detect differences in expression levels between two samples. A difference between the protein levels, or the mRNA in the two tissues that are compared, for example, in molecular weight, amino acid or nucleotide sequence, or relative abundance, indicates a change in the gene, or a gene that regulates it, in the tissue of the human that was suspected of being diseased.

The subject nucleic acid and/or polypeptide compositions may be used to analyze a patient sample for the presence of polymorphisms associated with a disease state or genetic predisposition to a disease state. Biochemical studies may be performed to determine whether a sequence polymorphism in an intermedin coding region or control regions is associated with disease, particularly diseases related to prolactin expression, hypertension, etc. Disease associated polymorphisms may include deletion or truncation of the gene, mutations that alter expression level, that affect the binding activity of the protein, the kinase activity domain, etc.

Changes in the promoter or enhancer sequence that may affect expression levels of intermedin can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express intermedin may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. Molecular Cloning: A Laboratory Manual, CSH Press 1989, pp. 14.2–14.33.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein(6-FAM),2,7-dimethoxy-4,5-dichloro-6-carboxyfluorescein (JOE), 6-carboxy-X-rhodamine (ROX), 6-carboxy-2,4,7,4, 7-hexachlorofluorescein (HEX), 5-carboxyfluorescein (5-FAM) or N,N,N,N-tetramethyl-6-carboxyrhodamine (TAMRA), radioactive labels, e.g. $^{32}$p, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g., amplified or cloned fragment, is analyzed by one of a number of methods known in the art. The nucleic acid may be sequenced by dideoxy or other methods, and the sequence of bases compared to a wild-type intermedin sequence. Hybridization with the variant sequence may also be used to determine its presence, by Southern blots, dot blots, etc. The hybridization pattern of a control and variant sequence to an array of oligonucleotide probes immobilized on an array, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in intermedins may be based on the functional or antigenic characteristics of the protein. Protein truncation assays are useful in detecting deletions that may affect the biological activity of the protein. Various immunoassays designed to detect polymorphisms in intermedin proteins may be used in screening. Where many diverse genetic mutations lead to a particular disease phenotype, functional protein assays have proven to be effective screening tools. The activity of the encoded intermedin protein in binding assays, etc., may be determined by comparison with the wild-type protein. Proteins may also be screened for the presence of post-translational modification of the intermedin proteins, e.g. under pathological conditions, including proteolytic fragments, amidation, acetylation etc.

Antibodies specific for intermedin may be used in staining or in immunoassays. Samples, as used herein, include biological fluids such as blood, cerebrospinal fluid, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal intermedin in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

In some embodiments, the methods are adapted for use in vivo. In these embodiments, a detectably-labeled moiety, e.g., an antibody, which is specific for intermedin is administered to an individual (e.g., by injection), and labeled cells are located using standard imaging techniques, including, but not limited to, magnetic resonance imaging, computed tomography scanning, and the like.

Diagnostic screening may also be performed for polymorphisms that are genetically linked to a disease predisposition, particularly through the use of microsatellite markers or single nucleotide polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. (1994) *Genomics* 24:225–233; Ziegle et al. (1992) *Genomics* 14:1026–1031; Dib et al., supra.

The detection methods can be provided as part of a kit. Thus, the invention further provides kits for detecting the presence of an mRNA encoding intermedin, and/or a polypeptide encoded thereby, in a biological sample. Procedures using these kits may be performed by clinical laboratories, experimental laboratories, medical practitioners, or private individuals. The kits of the invention for detecting a polypeptide comprise a moiety that specifically binds the polypeptide, which may be a specific antibody. The kits of the invention for detecting a nucleic acid comprise a moiety that specifically hybridizes to such a nucleic acid. The kit may optionally provide additional components that are useful in the procedure, including, but not limited to, buffers, developing reagents, labels, reacting surfaces, means for detection, control samples, standards, instructions, and interpretive information.

GENETICALLY ALTERED CELL or ANIMAL MODELS FOR INTERMEDIN FUNCTION

The subject nucleic acids can be used to generate transgenic animals or site specific gene modifications in cell lines. Transgenic animals may be made through homologous recombination, where the normal intermedin locus is altered. Alternatively, a nucleic acid construct is randomly integrated into the genome. Vectors for stable integration include plasmids, retroviruses and other animal viruses, YACs, and the like.

The modified cells or animals are useful in the study of intermedin function and regulation. For example, a series of small deletions and/or substitutions may be made in the intermedin gene to determine the role of different residues in receptor binding, signal transduction, etc. Of interest is the use of intermedin to construct transgenic animal models for stress related disorders, where expression of intermedin is specifically reduced or absent. Specific constructs of interest include anti-sense intermedin, which will block intermedin expression and expression of dominant negative intermedin mutations. A detectable marker, such as lac Z may be introduced into the intermedin locus, where up-regulation of intermedin expression will result in an easily detected change in phenotype.

One may also provide for expression of the intermedin gene or variants thereof in cells or tissues where it is not normally expressed or at abnormal times of development. By providing expression of intermedin protein in cells in which it is not normally produced, one can induce changes in cell behavior, e.g. in the control of lactation, vasodilation, etc.

DNA constructs for homologous recombination will comprise at least a portion of the intermedin gene with the desired genetic modification, and will include regions of homology to the target locus. The regions of homology may include coding regions, or may utilize intron and/or genomic sequence. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in culture. The transgenic animals may be any non-human mammal, such as laboratory animals, domestic animals, etc. The transgenic animals may be used in functional studies, drug screening, etc., to determine the effect of a candidate drug.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLE 1

Intermedin is identified as a novel member of the calcitonin/CGRP peptide family. Analysis of intermedin expression indicated that intermedin is expressed primarily in the pituitary and gastrointestinal tract. Intermedin increases cAMP production in SK-N-MC and L6 cells expressing endogenous CGRP receptors and competes with labeled CGRP for binding to its receptors in these cells. In addition, treatment of 293T cells expressing recombinant calcitonin receptor-like receptor (CRLR) and one of the three receptor activity modifying proteins (RAMPs) showed that a CRLR/RAMP receptor complex is required for intermedin signaling. In contrast to CGRP and ADM, which exhibit a preferential stimulation of CRLR when coexpressed with RAMP1 and RAMP2 or RAMP3, respectively, intermedin represents a nonselective agonist for the RAMP co-receptors. In vivo studies demonstrated that intermedin treatment leads to blood pressure reduction in both normal and spontaneously hypertensive rats via interactions with the CRLR/RAMP receptors. Furthermore, in vivo treatment in mice with intermedin leads to a suppression of gastric emptying activity and food intake. Thus, identification of intermedin as a novel member of the calcitonin/CGRP peptide family capable of signaling through the CRLR/RAMP receptor complexes provides an additional player in the regulation of peripheral tissues by CRLR, and will allow development of new therapeutic agents for pathologies associated with diverse vascular and gastrointestinal disorders.

Experimental Procedures

Cloning, phylogenetic analysis, and expression profiles of human intermedin. Human intermedin was initially identified from an EST and a genomic sequence (AK024788 and AL096767) and its identity was verified by PCR amplification using a human Marathon-ready pituitary cDNA library (Clontech, Inc., Palo Alto, Calif.). For analysis of intermedin mRNAs in the human digestive system, normalized first strand cDNA preparations were obtained from Clontech, Inc. The putative intermedin peptides from fish were deduced based on a zebrafish EST sequence (AW421384) and puffer fish genomic sequences (*Fugu rubripes* Scaffold_1011), respectively. The rat and mouse intermedin sequences were deduced based on EST BQ192607 and BG918210, respectively. Putative puffer fish αCGRP, α CGRP, ADM, and amylin were deduced based on puffer fish sequences Scaffold_9445, Scaffold_6549, JGI_28042, and JGI_8403, respectively. The BLOCK MAKER program (http://blocks.fhcrc.org) was used to align the mature peptides from different species. Phylogenetic analysis was carried out using a routine in ClustalW. The consensus secondary structure of calcitonin/CGRP family peptides was predicted using the Network Protein Sequence Analysis serve.

For Northern blotting analysis of intermedin expression, pituitary RNAs were extracted from pituitary glands obtained from male Sprague-Dawley rats. Following extraction using TriZol solution, total RNA was resolved using formaldehyde agarose gels and hybridized with a $^{32}$P-labeled rat intermedin cDNA probe. The x-ray film was exposed at −80C for one week with intensifying screens.

Peptide synthesis. Intermedin-related peptides were synthesized based on the solid phase fluorenylmethoxycarbonyl protocol and analyzed by reverse phase HPLC with Vydac C18 analytical column and mass spectrometry using a MALDI-TOF Voyager-DE RP Workstation. Synthetic ADM, α CGRP, and related peptides were obtained from Sigma-Aldrich Corp. (St. Louis, Mo.), AnaSpec, Inc. (San Jose, Calif.), and Bachem (Torrance, Calif.). Radiolabeled $^{125}$I-CGRP (2,000 Ci/mmole) was from Amersham Pharmacia (Arlington Heights, Ill.). Stocks of different hormones were prepared in distilled water and diluted in culture medium.

Immunoanalysis. Rabbit anti-intermedin antibodies were generated using synthetic peptides corresponding to residues 28–47, MGPAGRQDSAPVDPSSPHSY, of human intermedin (Strategic Biosolutions, Ramona, Calif.). This peptide antigen was selected based on the high sequence identity (85%) found in this region of human and rodent intermedins and the negligible similarity with other family peptides. The intermedin peptide was conjugated to the keyhole limpet hemocyanin using 1-ethyl-3-(3-dimethylaminopropyl) carbodiimide hydrochloride before immunization. Antibodies were purified using antigen-conjugated affinity columns. In immunoblot analysis, the anti-human intermedin antibody cross-reacted with synthetic intermedin counterparts from different vertebrates but not paralogous peptides including calcitonin, CGRP, ADM, and amylin. For immunohistochemical analysis, tissues were obtained from adult rats, mice, and bullfrogs, and analyzed as described. To demonstrate that intermedin transcript encodes the predicted intermedin mature peptide, full-length human intermedin cDNA was subcloned into the pcDNA3.1 expression vector. For Western blotting analysis of intermedin in culture media, 293T cells were transfected with the intermedin expression vector using the calcium phosphate precipitation method. Forty-eight hours after transfection, serum-free culture media were harvested and concentrated using a Centricon 3 column. After concentration, the supernatant was boiled for 5 min in denaturing buffer with 100 mM dithiothreitol before SDS-PAGE and Western blotting analysis using anti-intermedin antibodies.

Stimulation of cAMP production in SK-N-MC and L6 cells by intermedin and related peptides. Human neuroblastoma SK-N-MC and rat L6 skeletal myoblast cells expressing endogenous CRLR were obtained from American Type Culture Collection. To estimate adenylyl cyclase activation, SK-N-MC and L6 cells ($2\times10^5$ viable cells/well) were plated in 24-well culture dishes in DMEM/F12 medium one day before treatment. Following 2 h incubation in serum-free DMEM/F12 medium, cells were treated with testing reagents for 30 min in medium containing 0.1% BSA and 2.5 mM 3-isobutyl-1-methylxanthine (IBMX, Sigma-Aldrich Corp.) to prevent hydrolysis of cAMP by phosphodiesterases. Following treatment, cells were lysed and cAMP content determined by a specific radioimmunoassay.

Activation of CRLR/RAMP receptor complexes by intermedin in transfected 293T cells. To study the interaction between intermedin and the CRLR/RAMP receptor complexes, we cloned human CRLR, RAMP1, RAMP2, and RAMP3 (accession numbers NP_005786, NP_005846, NP_005845, and O60896, respectively) cDNAs by PCR from human Marathon-ready cDNA libraries using two sets of primers flanking the full-length coding sequences of each gene. Each cDNA was verified by DNA sequencing and subcloned into the expression vector pcDNA3.1. To allow the detection of cell surface expression of these proteins, CRLR and RAMP proteins were tagged at the N-terminus of the mature protein with a FLAG epitope. Because it has been shown that epitope tagging affects the signaling by RAMP1 protein, we used the wild type RAMP1 construct for the analysis of intermedin signaling. HEK293T cells were maintained in 35-mm culture dishes in DMEM/Ham's F-12 (Life Technologies, Inc.) supplemented with 10% FBS, 100 $\mu$g/ml penicillin, 100 $\mu$g/ml streptomycin, and 2 mM L-glutamine. The cells were co-transfected with 10 $\mu$g CRLR and/or 10 $\mu$g RAMP expression plasmid using the calcium phosphate precipitation method. Forty-eight hours after transfection, cells were washed twice with Dulbecco's PBS (D-PBS), harvested from culture dishes, and centrifuged at 400×g for 5 min. To determine the level of expression of CRLR and RAMP on the cell surface, the resuspended cells ($2\times10^6$/tube) were incubated with the FLAG M1 antibody (50 mg/ml) (Sigma-Aldrich Corp.) in Tris-buffered saline (pH 7.4) containing 5 mg/ml bovine serum albumin and 2 mM $CaCl_2$(assay buffer) for 4 h at room temperature in siliconized tubes. Cells were then washed twice with 1 ml of assay buffer after centrifugation at 14,000×g for 15 sec. The horseradish peroxidase-conjugated secondary antibody (sheep anti-mouse IgG) was added to the resuspended cell pellets and incubated for 1 h at room temperature. Cells were washed twice with 1 ml of assay buffer by repeated centrifugation before determination of horseradish peroxidase activity in cell pellets using the ECL reagents (Amersham Bioscience) and a Lumimark microplate reader (Bio-Rad, Inc.). Background binding was determined by adding excess amounts of the synthetic FLAG peptide (Sigma-Aldrich Corp.) at a concentration of 100 $\mu$g/ml. For the assay of adenylyl cyclase activation in transfected cells, cells ($2\times10^5$/ml) were placed in 24-well tissue culture plates (Corning, Inc. Corning, N.Y.) and preincubated at 37C for 30 min in the presence of 2.5 mM IBMX before hormonal treatment for 4 h.

Receptor-binding assay. Ligand-binding assays were done in siliconized microfuge tubes at 37C for 2 h. Intact SK-N-MC and L6 cells were resuspended in the binding buffer (20 mM Tris-HCl, pH 7.4, 2 mM $MgCl_2$, and 0.1% BSA) with 0.06 $\mu$g of $^{125}$I-CGRP and various concentrations of nonradioactive peptides. After a 2 h incubation at 37C, the cell-associated ligand was estimated. Radioactivity was determined using a $\gamma$-counter (EG&G Wallace, Gaithersburg, Md.).

Effects of intermedin on blood pressure and heart rate in normal and hypertensive rats. Blood pressure measurements in conscious male Sprague-Dawley rats and spontaneously hypertensive rats (SHR)(7–9 weeks of age) were made in animals preadapted to the measurement procedure. Indirect systolic pressure was determined by a programmable NIBP system using the tail-cuff method (Columbus Instruments, Columbus, Ohio). Following attachment of the pressure transducer, rats were left undisturbed for 10 min before baseline measurements that spanned a 15-min interval. Following baseline measurements, rats were injected intraperitoneally with varying doses of hormones. Blood pressure and heart rate were monitored for 40 min at 20-sec intervals. Changes in blood pressure were calculated as the average of thirty measurements performed within each 10-min interval.

Effects of intermedin on gastric emptying activity. Eight-week-old C57/BL6 male mice deprived of food for 20 h were given food pellets for 90 min before intraperitoneal injection with different hormones or saline. After treatment, mice were deprived of food again and killed 90 min later. The stomach was excised at the pylorus and cardia before weighing. Gastric emptying was calculated by comparing the stomach weight of treated mice to the stomach weight of control mice killed at the time of hormone injection.

Analysis of ingestive behavior. Eight-week-old C57/BL6 male mice were housed individually in a regulated environment. Before intraperitoneal injection with testing reagents, mice were deprived of food for 20 h with free access to water. Food intake was measured by placing preweighed pellets in the cage and weighing uneaten pellets at 1, 2, and 4 h after treatment.

Statistical analysis. Differences between treatment groups were analyzed using ANOVA and Student's t-test.

Results

Intermedin as a calcitonin/CGRP family peptide. We searched GenBank databases for sequence motifs with unique primary and secondary structures shared by all calcitonin/CGRP family peptides using a phylogenetic profiling approach that has allowed the identification of novel CRH family peptides. Candidate sequences were screened for the presence of proteolytic cleavage sites flanking the putative mature region of the precursor proteins. Based on these criteria, we have identified intermedin genes from mammals and teleosts including zebrafish and a Japanese puffer fish (Takifugu rubripes). Human intermedin encodes a prepro-protein of 148 amino acids with a signal peptide for secretion at the N-terminus (FIG. 1A). Although the overall amino acid sequence of intermedin showed no similarity to known proteins, a stretch of 47 residues at the C-terminus is flanked by dibasic proteolytic cleavage sites at the N-terminus and an alpha-amidation donor residue at the C-terminus. The putative mature region of intermedin shares approximately 28% sequence identity with ADM and <20% with CGRP (FIG. 1B).

Importantly, the predicted mature region adopted an amino-terminal disulfide-bonded loop leading into an alpha-helix followed by a disordered structure that is shared by all calcitonin/CGRP family peptides (FIG. 1B). Furthermore, sequence alignment of intermedin precursors from mammals and teleosts indicated that sequence conservation in orthologous intermedins is restricted to the mature region. The mature intermedins of human and fish share a >60% similarity whereas human and rodent intermedins are 87% identical (FIG. 1B).

In addition, the mouse and rat intermedin peptides appeared to differ by only one amino acid. Furthermore, analysis of orthologous intermedin indicated that the position of N-terminal dibasic cleavage sites varied by a few amino acids among different species whereas an arginine residue seven amino acids downstream of the dibasic cleavage motif of human intermedin is conserved in all species, suggesting that the mature intermedin from human and other species could be a 40-amino-acid peptide. On the basis of these sequence analyses, we predicted that a 47-amino-acid mature peptide (intermedin-long or IMDL) and a shorter 40-amino-acid intermedin (intermedin-short or IMDS) could be generated by proteolytic cleavage at the N-terminal proximate basic residues followed by an amidated C-terminus. Because the putative prepro-region of intermedin from diverse vertebrates is not conserved, intermedin is unlikely to encode additional active peptides such as the proADM N-terminal 20 peptide (PAMP) found in the ADM precursor.

Figure 1C:
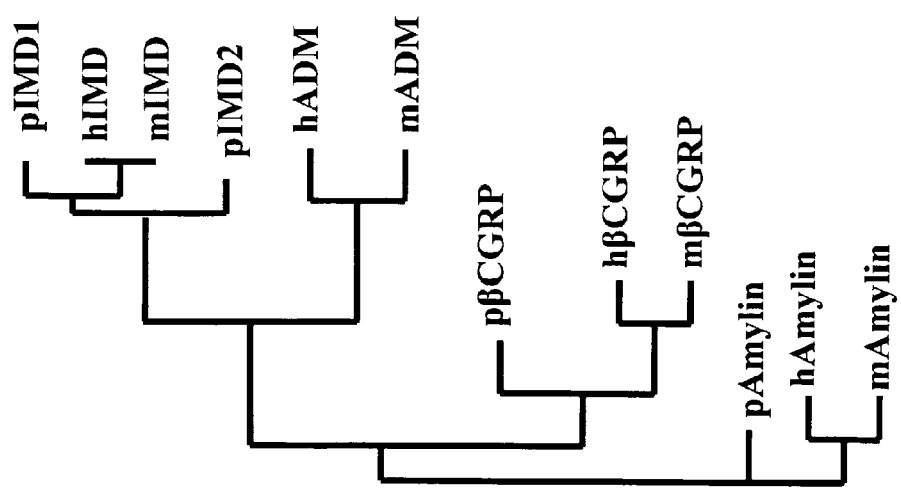

Phylogenetic analysis of twelve CGRP family peptides from fish and mammals suggested an ancient evolution for three subgroups of these peptide hormones with mammalian and teleost intermedins clustered in a separate branch with ADM and CGRP (FIG. 1C). Thus, intermedin and other family peptides evolved before the emergence of modern teleosts and tetrapods. Genomic analysis showed that intermedin is located on the distal arm of human chromosome 22q13 and syntenic mouse chromosome 15. In both human and mouse genomes, intermedin neighbors an aldehyde reductase-like gene. In contrast, all other calcitonin/CGRP family genes cluster on human chromosomes 11 and 12.

Figure 2A:
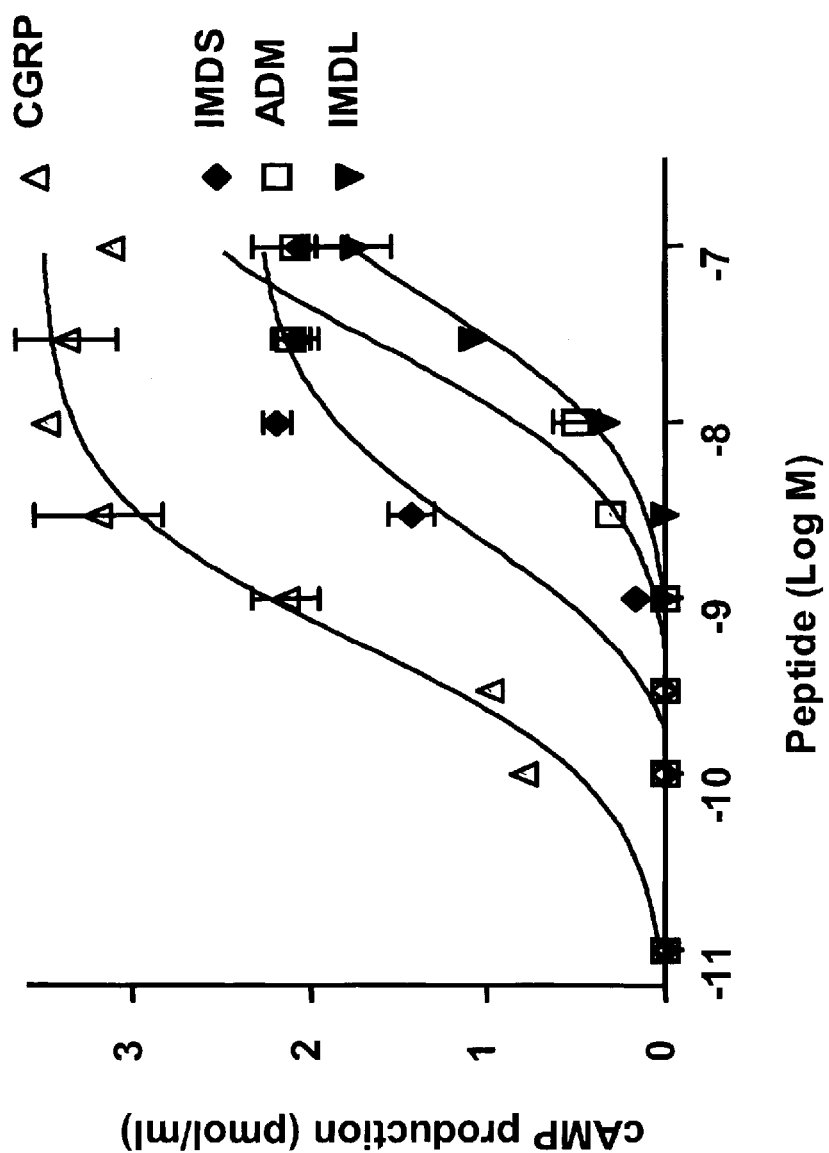
FIGS. 2A–2F. Intermedin shares receptors with CGRP and ADM. A. and B. Synthetic intermedin peptides (IMDL and IMDS) stimulate cAMP production in human neuroblastoma SK-N-MC cells (A) and rat L6 skeletal myoblast cells (B). No stimulation by a nonamidated form of intermedin, a truncated amidated intermedin fragment (intermedin 17–47, IMD 17–47), or a 31-amino-acid peptide from the prepro-region of intermedin (prointermedin 55–85, proIMD 55–85) was observed. Data are mean ±s.e.m. (N=4). C. Blockage of the stimulatory effect of intermedin on cAMP production by a CGRP receptor antagonist, CGRP8–37, in L6 cells. D. Blockage of the stimulatory effect of intermedin by IMD17–47 (1 μM) and the anti-intermedin antibody (anti-IMD Ab) in L6 cells. Data are mean±s.e.m. (N=4). No effect was observed by cotreatment with an anti-SRP/urocortin II antibody (anti-SRP Ab). *, significantly different from controls (P<0.05). E. and F. Competitive displacement by unlabeled intermedin and related peptides of $^{125}$I-CGRP bound to SK-N-MC (E) or L6 (F) cells. Data are mean±s.e.m. (N=3).
Figure 2B:
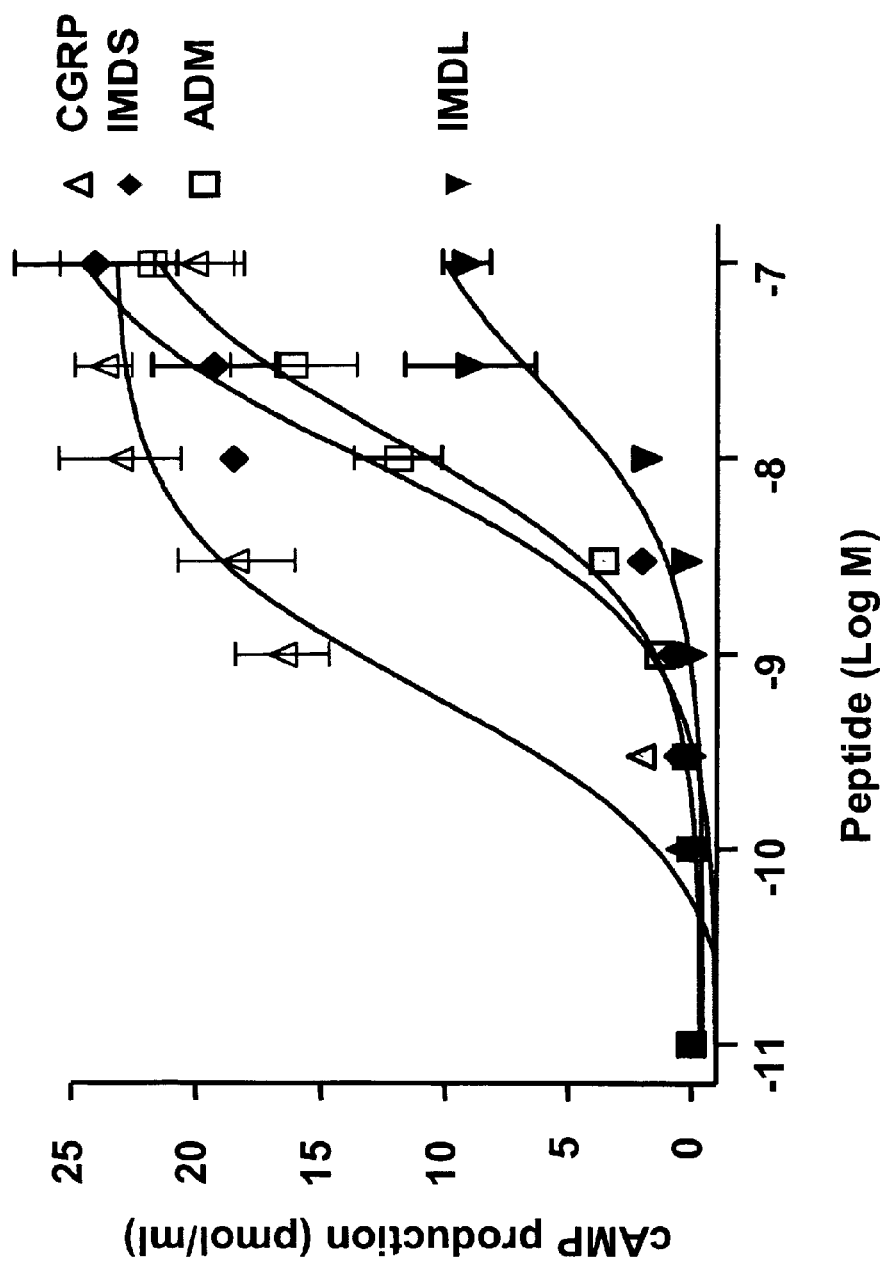

Intermedin activates the cAMP-dependent pathway in SK-N-MC and L6 cells via the CGRP receptor. Pairwise sequence comparison and phylogenetic tree building based on all GPCR sequences indicated that intermedin is closest to ADM and CGRP whereas no orphan GPCR shares a close relatedness to CRLR, the receptor for ADM and CGRP. Thus, CRLR is a candidate receptor for intermedin. To test this hypothesis, we treated human neuroblastoma-derived SK-N-MC cells and rat L6 skeletal myoblast cells, known to express different levels of CRLR and RAMPs, with synthetic intermedin peptides, and then monitored cAMP production. As shown in FIGS. 2A and 2B, treatment with amidated long intermedin peptide (amino acid 1–47, IMDL) or short intermedin (amino acid 8–47, IMDS) resulted in dose-dependent increases of cAMP production in both cell lines. The observed activation is specific as treatments with a nonamidated form of intermedin, a truncated amidated intermedin fragment (intermedin17–47, IMD17–47), or a 31-amino-acid peptide from the prepro-region of human intermedin (prointermedin55–85) have no effect in either cell line, suggesting that α-amidation and residues 8–16 of intermedin are important for intermedin bioactivity.

Figure 2C:
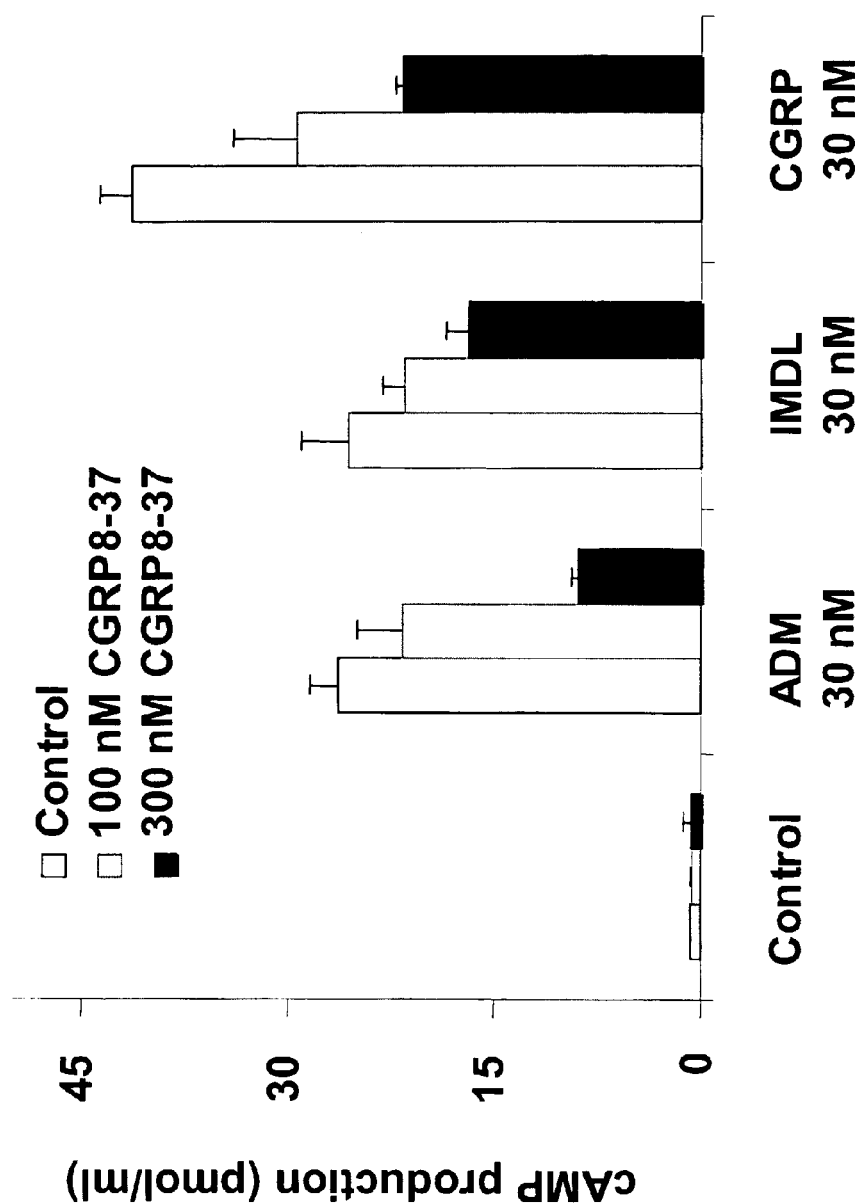
Figure 2D:
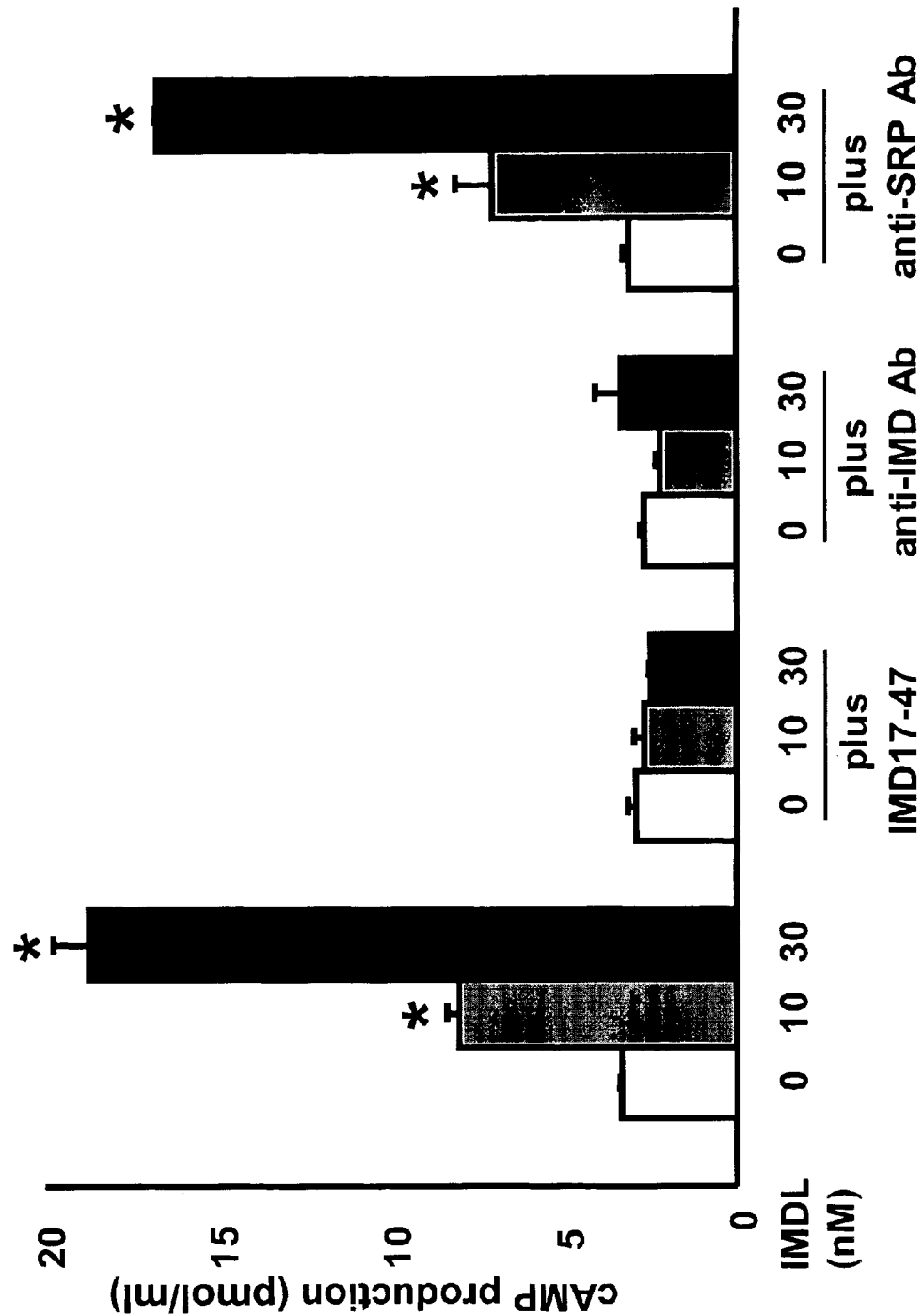

Consistent with earlier reports, both ADM and a CGRP also stimulated cAMP production in these cell lines (FIGS. 2A and 2B). Of importance, the stimulatory effect of intermedin was suppressed by cotreatment with a CGRP receptor antagonist, CGRP8–37, in L6 cells (FIG. 2C) demonstrating that intermedin activates the cAMP-dependent pathway via the CGRP receptor. To further characterize the specific action of intermedin on cAMP production, L6 cells were cotreated with a putative intermedin C-terminal receptor-binding domain, IMD17–47, or an anti-intermedin polyclonal antibody. As shown in FIG. 2D, IMD17–47 was found to be a functional antagonist of intermedin action, consistent with the observed antagonistic effect of N-terminally truncated CGRP8–37 (FIG. 2C). In addition, cotreatment with the anti-intermedin antibody blocked the stimulatory effect of intermedin whereas cotreatment with an antibody raised against the unrelated stresscopin-related peptide (SRP)/urocortin II had no effect (FIG. 2D).

Figure 2E:
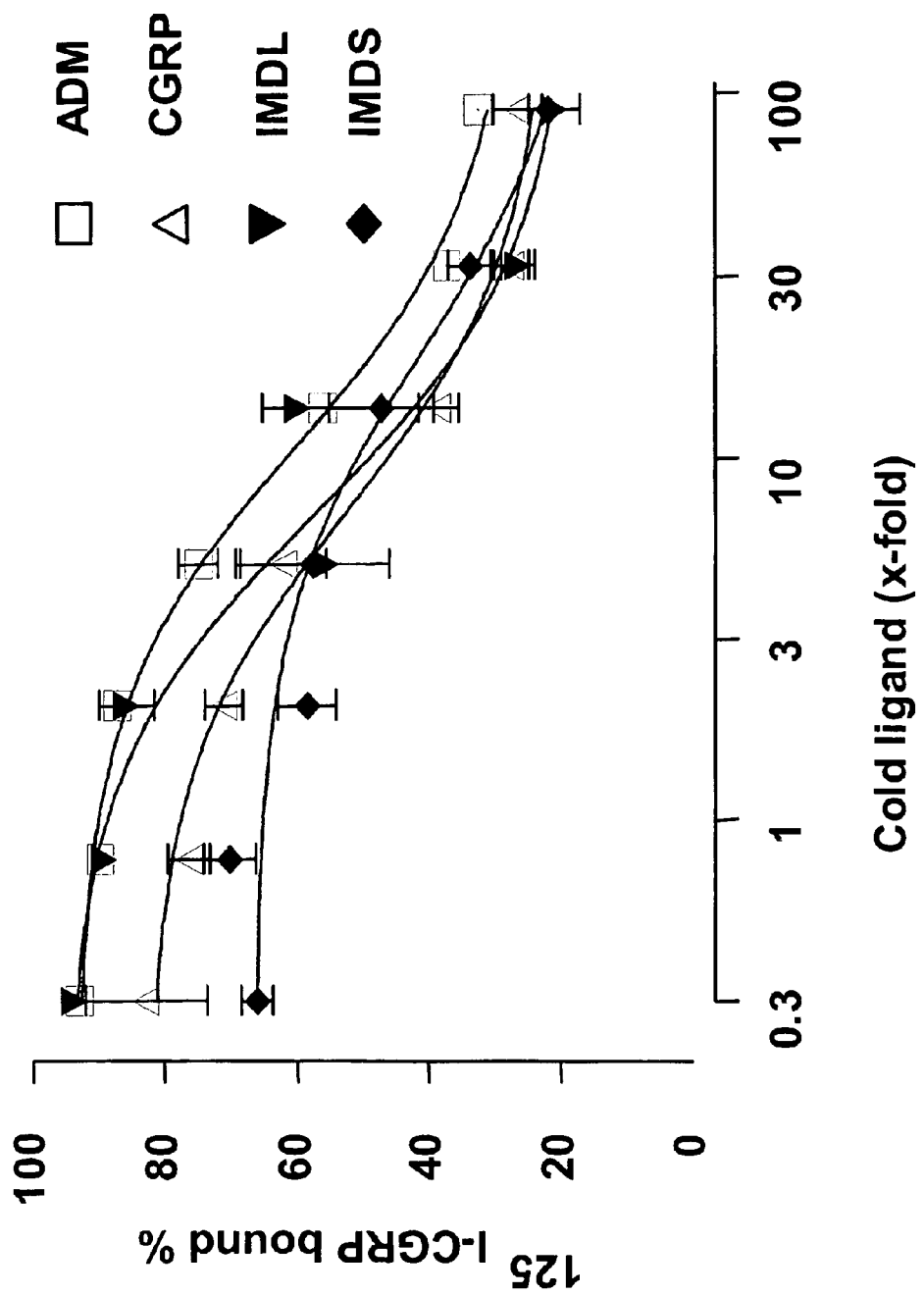
Figure 2F:
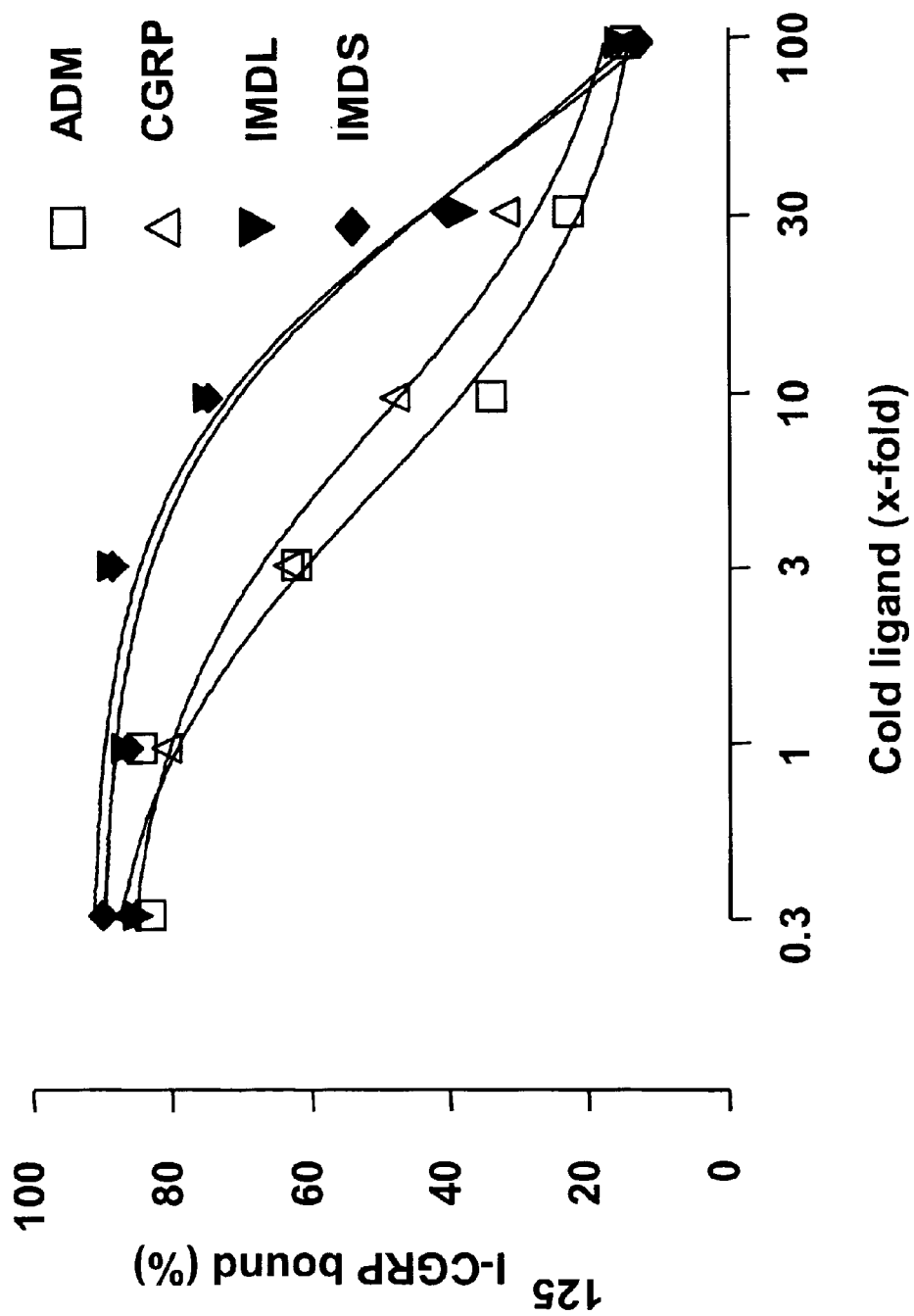

To establish a direct interaction between intermedin and CRLR, we used iodinated CGRP as the radioligand for receptor-binding assays. As shown in FIGS. 2E and 2F, IMDL and IMDS displaced $^{125}$I-CGRP binding to the SK-N-MC and L6 cells dose-dependently.

Figure 3:
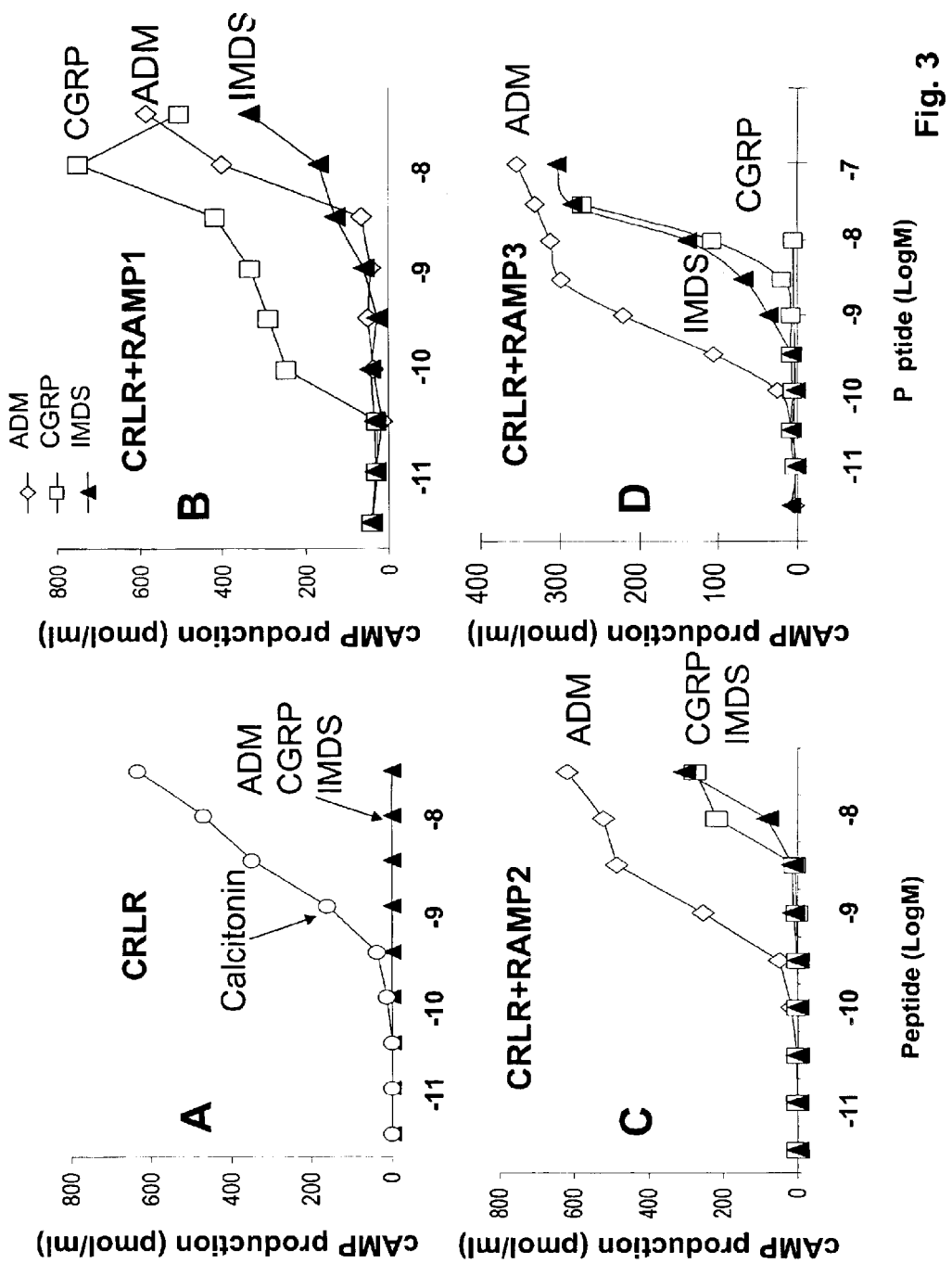
FIGS. 3A–3E. Intermedin activates recombinant CRLR/RAMP receptor complexes in transiently transfected 293T cells. A–D. Treatment of 293T cells transiently transfected with an empty expression vector or a CRLR expression vector with intermedin, CGRP, or ADM has no effect on the whole cell cAMP production (A). In contrast, calcitonin increases cAMP production dose-dependently through the endogenous calcitonin receptor. Unlike cells expressing CRLR solely, treatment of intermedin increases cAMP production in cells expressing CRLR with RAMP1 (B), RAMP2(C), or RAMP3 (D). Likewise, treatment of CGRP or ADM stimulates cAMP production in cells expressing CRLR/RAMP receptor complexes with different potency (FIGS. 3B–3D, N=3). E. Indirect binding analysis of cell surface expression of CRLR and RAMP proteins using horseradish peroxidase-conjugated sheep anti-mouse antibodies and anti-FLAG epitope antibodies. Expression of FLAG epitope-tagged CRLR and RAMPs on the cell surface of transfected cells is increased by cotransfection of CRLR and RAMP expression vectors as compared to transfection with a single expression vector encoding CRLR or RAMP.
Figure 3:
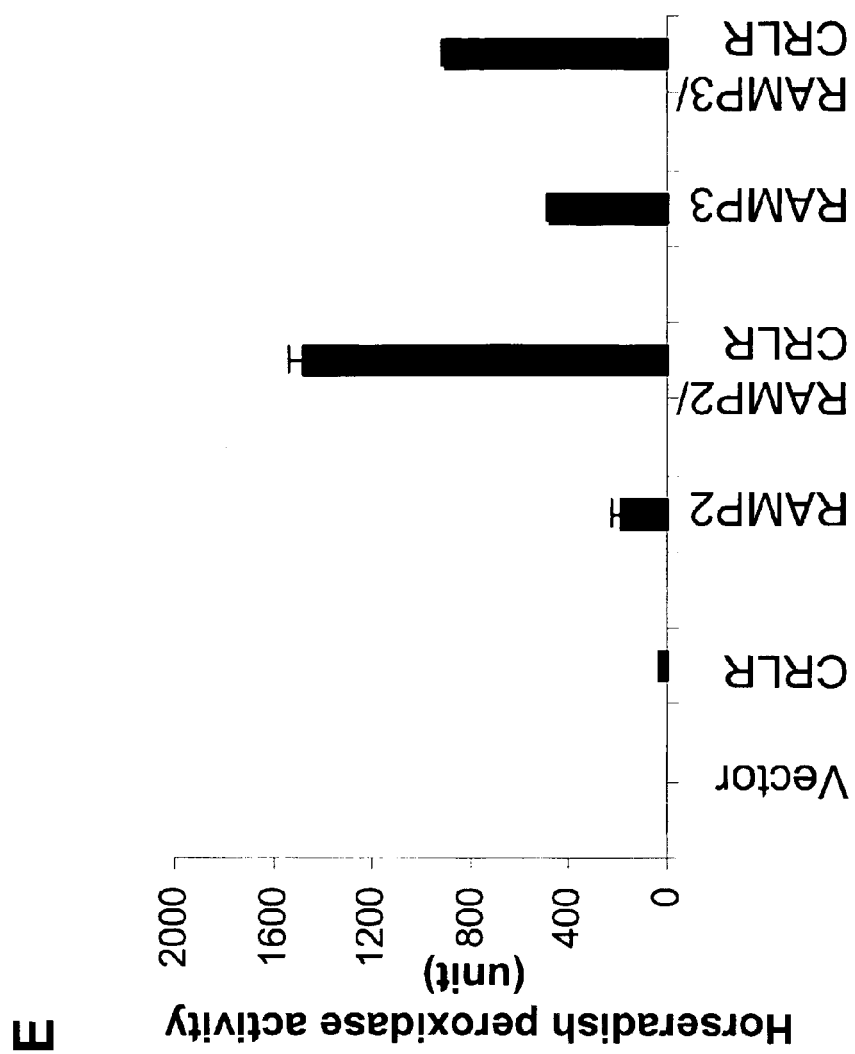

Intermedin is a nonselective agonist for CRLR/RAMP receptor complexes. CGRP and adrenomedullin mediate their action through the CRLR/RAMP complexes consisting of CRLR and one of the three RAMP polypeptides. To investigate the role of CRLR/RAMP receptor complexes in intermedin signaling, we treated 293T cells expressing different combinations of recombinant CRLR and/or RAMP proteins with intermedin and related peptides. As shown in FIG. 3A, treatment of intermedin, CGRP, or ADM has no effect on the cAMP production in 293T cells expressing CRLR alone whereas calcitonin increases cAMP dose-dependently via the endogenous calcitonin receptor. In contrast, intermedin stimulates cAMP production in cells expressing different CRLR/RAMP receptor complexes dose-dependently (FIGS. 3B–3D). Consistent with earlier studies, CGRP and ADM exhibit a preferential stimulation of CRLR when coexpressed with RAMP1 and RAMP2 or RAMP3, respectively. As compared to CGRP, intermedin exhibits a greater potency in the stimulation of cAMP production in cells expressing CRLR/RAMP3, but has lower activity on the CRLR/RAMP1 complex. In contrast, intermedin has a lower potency on the activation of both CRLR/RAMP2 and CRLR/RAMP3 as compared to adrenomedullin. Thus, the overall rank of potency for the stimulation of CRLR/RAMP1, CRLR/RAMP2, and CRLR/RAMP3 are CGRP>IMD=ADM, ADM>IMD=CGRP, and ADM>IMD>CGRP, respectively. Further, consistent with earlier reports, the expression of CRLR/RAMP receptors on the cell surface of transfected cells was found to be increased synergistically by coexpressing CRLR and RAMP proteins (FIG. 3E).

Figure 4:
FIGS. 4A–4K. Expression of intermedin in the pituitary. A. Northern blotting analysis showed that two specific intermedin transcripts are expressed in rat pituitary cells. Positions for 28S and 18S RNA are indicated by arrows. B. Western blotting analysis of synthetic peptides using an anti-intermedin antibody generated against the C-terminal twenty amino acids of human intermedin, (SEQ ID NO:2, residues 104–124) MGPAGRQDSAPVDPSSPHSY. The anti-intermedin antibody is specific for intermedin and shows no cross-reaction with CGRP, calcitonin, ADM, or amylin. Molecular weight markers are shown on the left and specific bands are indicated by arrows. C–F. Immunohistochemical staining of mouse pituitary sections using the anti-intermedin antibody (C, X100; D, X200), preimmune rabbit serum (E), or anti-intermedin antibody presaturated with the intermedin ligand (F). Sections incubated with preimmune serum (E) or antibodies presaturated with the intermedin peptide antigen (F) showed negligible signals. G and H. Immunohistochemical analysis of intermedin expression in pituitary sections of rat (G) and bullfrog (H). I and J. Immunohistochemical staining of mouse pituitary sections using an anti-melanin-stimulating hormone (MSH) antibody (I) or the anti-intermedin antibody presaturated with an MSH peptide (J). Specific signals are indicated by arrows. AL, anterior lobe; IL, intermediate lobe; PL, posterior lobe. K Western blotting analysis of concentrated culture media from 293T cells transfected with an intermedin expression vector. The anti-intermedin antibody detected an approximately 5 kDa mature intermedin peptide in culture media whereas media from cells transfected with the empty vector displayed no signal. Specific intermedin signals are indicated by an arrow. Positive signals from the synthetic intermedin peptide are shown on left lanes.
Figure 4:
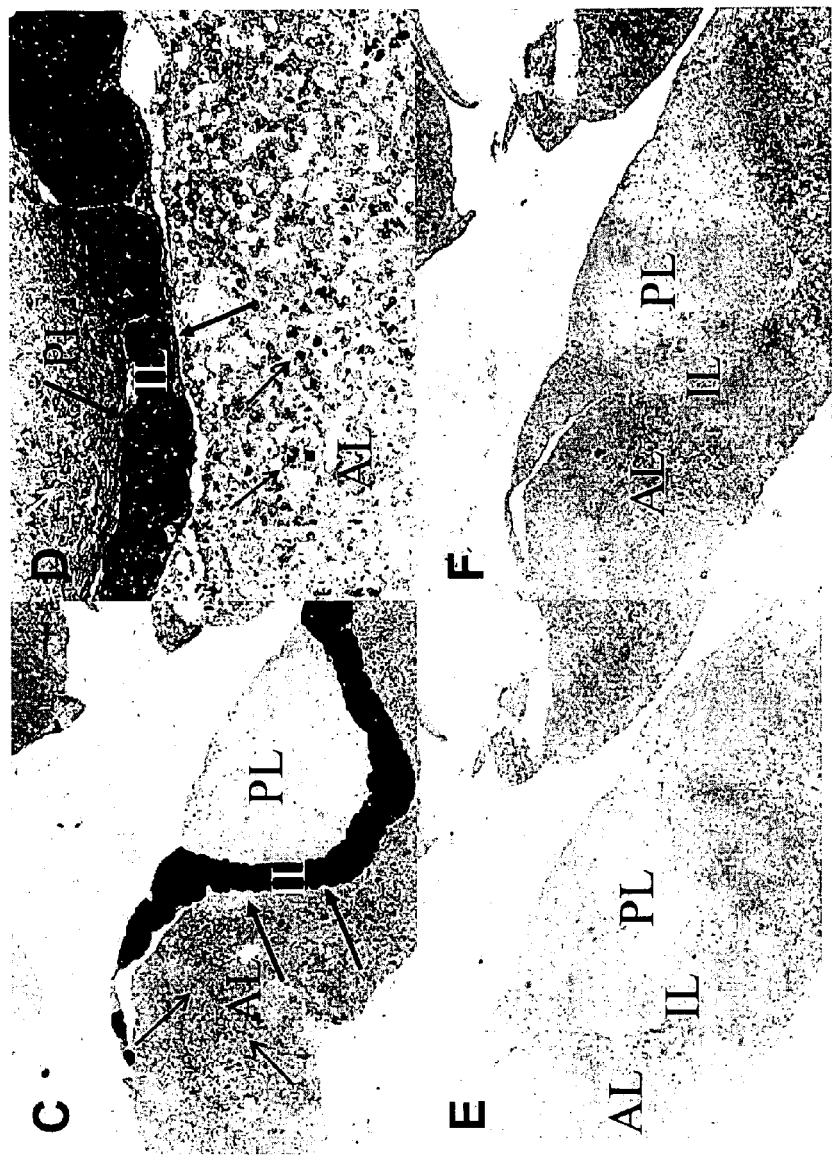
Figure 4:
Figure 4:
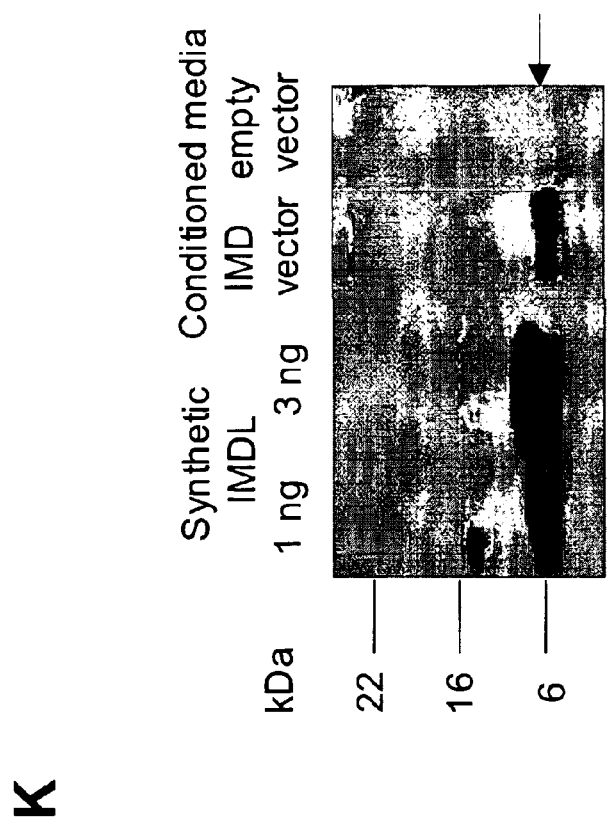

Intermedin expression in the pituitary and stomach. Initial RT-PCR analysis showed that the intermedin transcript is expressed in the pituitary and stomach. Northern blotting analysis of rat pituitary RNA showed that two specific intermedin transcripts of approximately 5 and 2.5 kb are present in the pituitary (FIG. 4A). To further characterize the expression profile of intermedin, four independent antibodies were developed using a C-terminal 20-amino-acid intermedin peptide (IMD28–47). As shown in FIG. 4B, the anti-intermedin antibody (C2411–2) is specific for intermedin and shows no cross-reaction with related peptides including calcitonin, CGRP, ADM, or amylin. Using the specific anti-intermedin antibody, immunohistochemical analysis of more than twenty different mouse tissues confirmed intermedin expression in the pituitary and the stomach. As shown in FIGS. 4C (X100) and 4D (X200), intermedin is expressed mainly in the intermediate lobe of the pituitary with sporadic signals in the anterior lobe. In contrast, negative controls using preimmune serum or anti-intermedin antibodies presaturated with the intermedin antigen showed no specific signals (FIGS. 4E and 4F). Likewise, immunohistochemical analysis of pituitary sections from rats and bullfrogs showed that intermedin expression is restricted to the intermediate and anterior lobes of pituitary (FIGS. 4G and 4H). Because melanin-stimulating hormone (MSH) has a similar expression pattern in pituitary (FIG. 4I, anti-MSH staining), we tested whether the anti-intermedin antibody cross-reacts with the MSH peptide.

Figure 5:
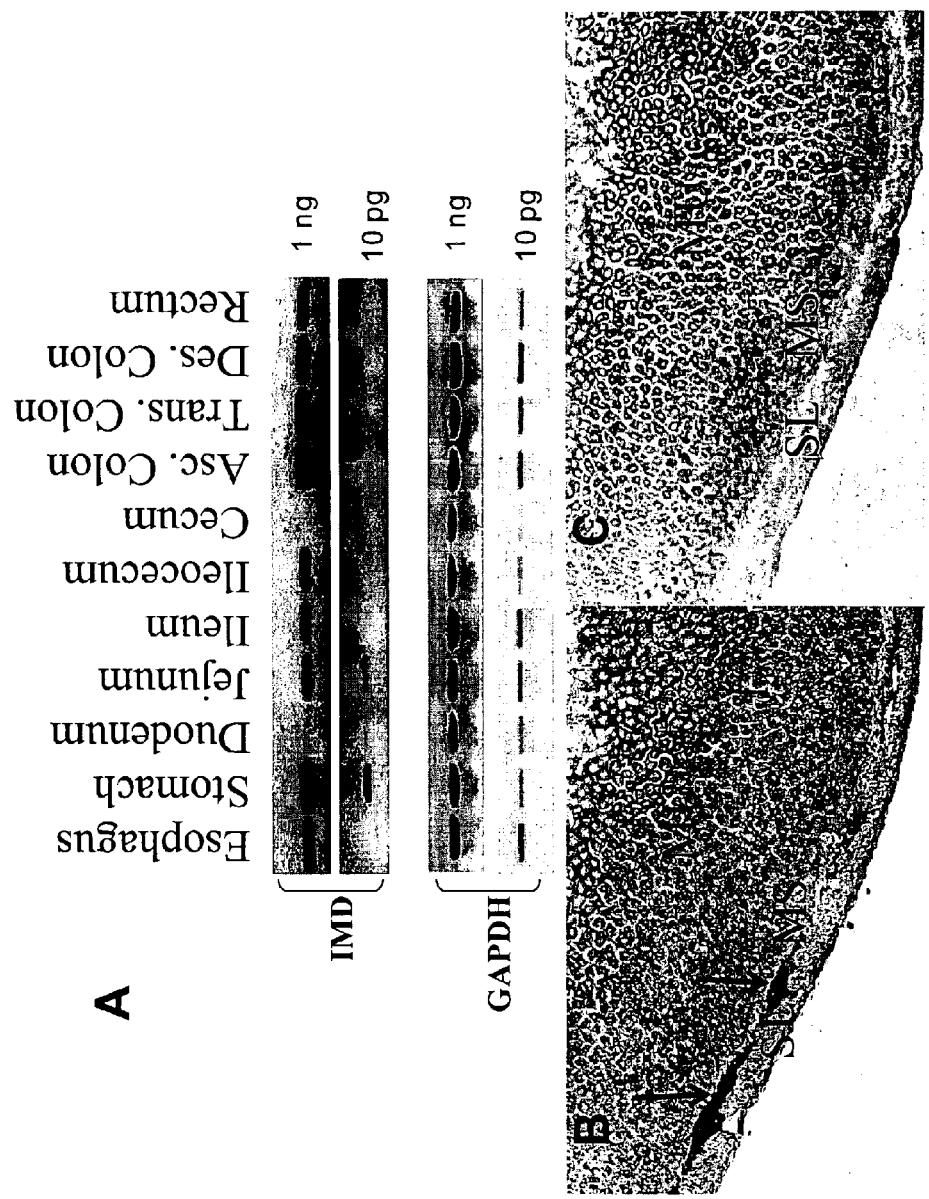
FIGS. 5A–5C. Expression of intermedin in digestive tissues. A. For the analysis of intermedin mRNAs in the human digestive system, normalized first strand cDNA preparations from human esophagus, stomach, jejunum, duodenum, ileum, ileocecum, cecum, ascending colon, descending colon, transverse colon, and rectum (higher panel, 1 ng template/reaction; lower panel, 10 pg template/reaction) were obtained from Clontech Inc. Specific bands (303 bp) were PCR-amplified using intermedin gene-specific primer pairs under high-stringency conditions. The primer sequences for intermedin PCR analysis are: forward (SEQ ID NO:3) 5'-AGGGAGGGGAACTCAGCAGTTCAGGAG-3' and reverse (SEQ ID NO:4) 5'-GTTCTTGTTCTTGCTGTCACTTGGGCCT-3'. The expression of GAPDH transcripts in different cDNA templates was also analyzed to assess the quality of the cDNA templates (higher panel, 1 ng template/reaction; lower panel, 10 pg template/reaction). Immunohistochemcal staining of mouse stomach sections showed that intermedin is found primarily in the muscularis mucosae layer of stomach (B) and the signal is abolished by presaturation with the intermedin antigen (C). Specific signals are indicated by arrows. MU, mucosal layer; MS, muscularis layer; SL, serosal layer.

As shown in FIG. 4J, the specific staining of intermedin in the pituitary was not abolished by preincubating with an MSH peptide. To further demonstrate that the intermedin mRNA encodes the predicted mature intermedin peptide, a human intermedin cDNA was subcloned in the eukaryotic expression vector pcDNA3.1, and the expression of intermedin peptide from this construct was investigated using transfected 293T cells. Western blotting analysis of concentrated culture media showed that cells transfected with the intermedin expression vector secretes an approximately 5 kDa mature intermedin peptide into the culture media whereas culture media from cells transfected with the empty vector display no signal (FIG. 4K). To characterize the expression of intermedin in the gastrointestinal tract, a panel of human cDNA from the gastrointestinal tract was analyzed by PCR. As shown in FIG. 5A (upper panel, 1 ng cDNA template/tube), the expression of the intermedin transcript could be detected in the esophagus, stomach, jejunum, ileum, ileocecum, ascending colon, transverse colon, descending colon, and rectum. PCR analysis using a lower amount (10 pg/tube) of cDNA templates showed that the expression of the intermedin transcript is greater in the stomach and jejunum (FIG. 5A, lower panel). Further, immunohistochemcal staining showed that intermedin is found primarily in the muscularis mucosae layer of stomach (FIG. 5B) and the signal is abolished by presaturation with the intermedin antigen (FIG. 5C).

Figure 6A:
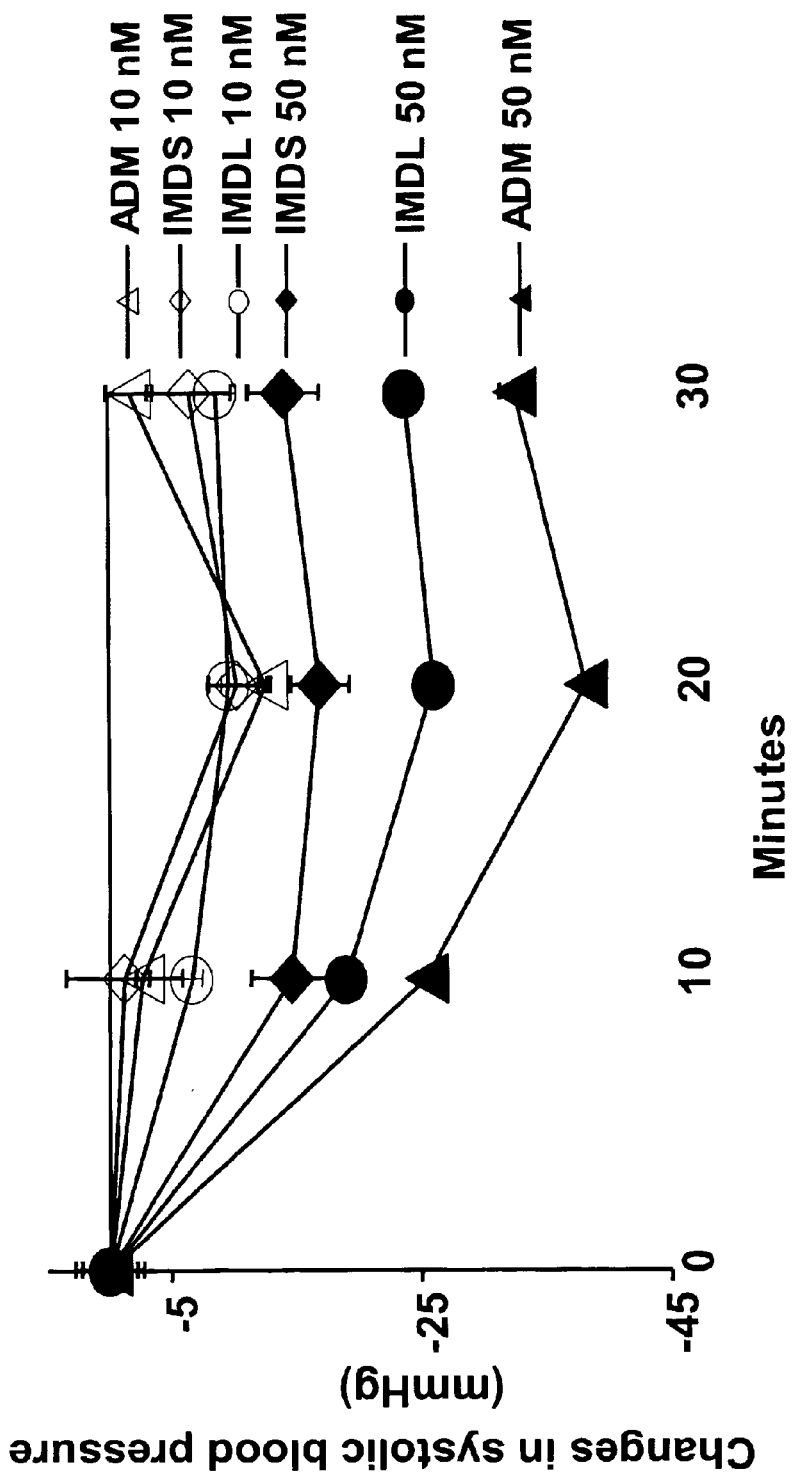
FIGS. 6A–6D. Decrease of systemic blood pressure and increase of heart rate by intermedin and related peptides. A.
Figure 6B:
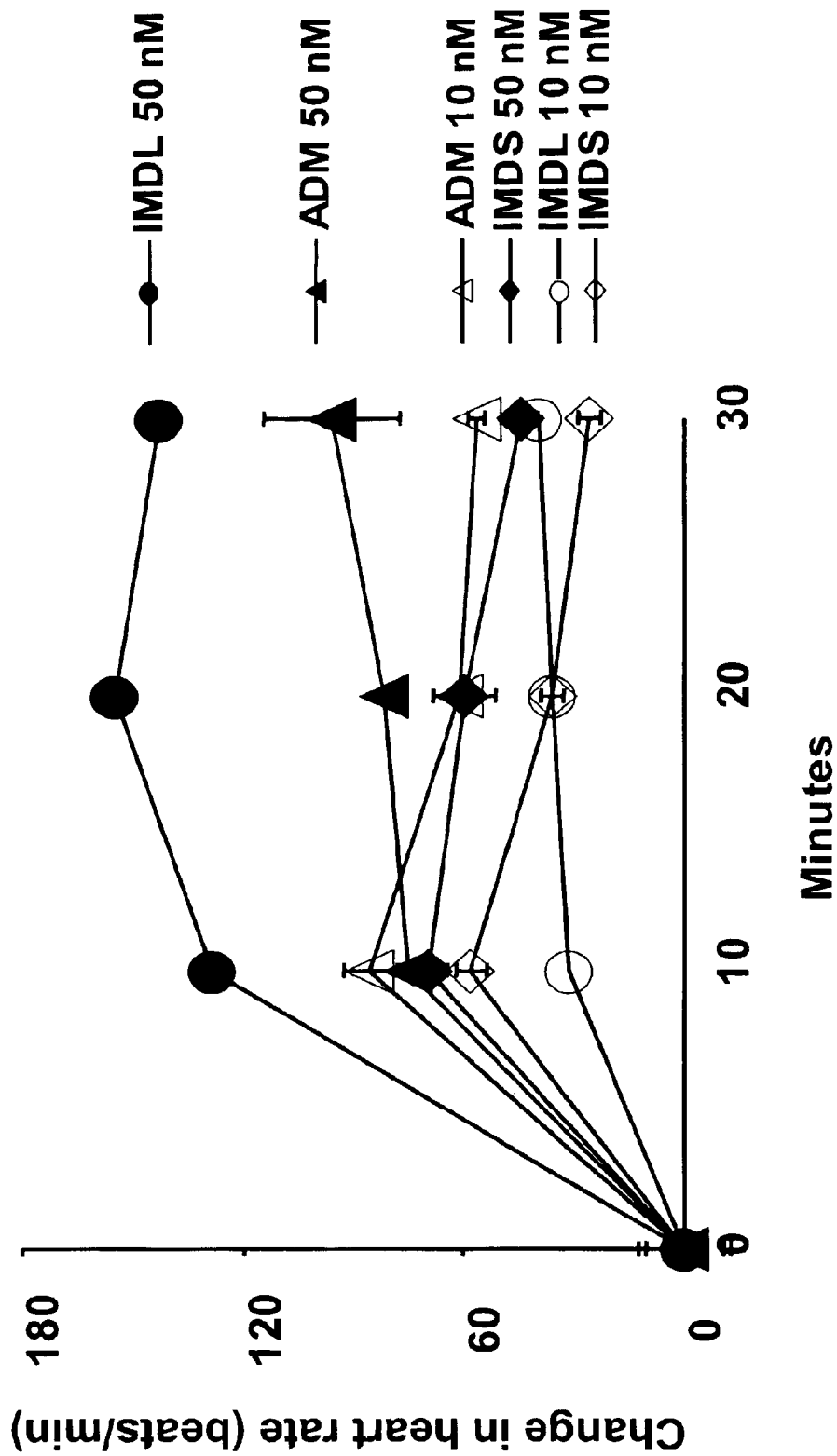
Figure 6C:
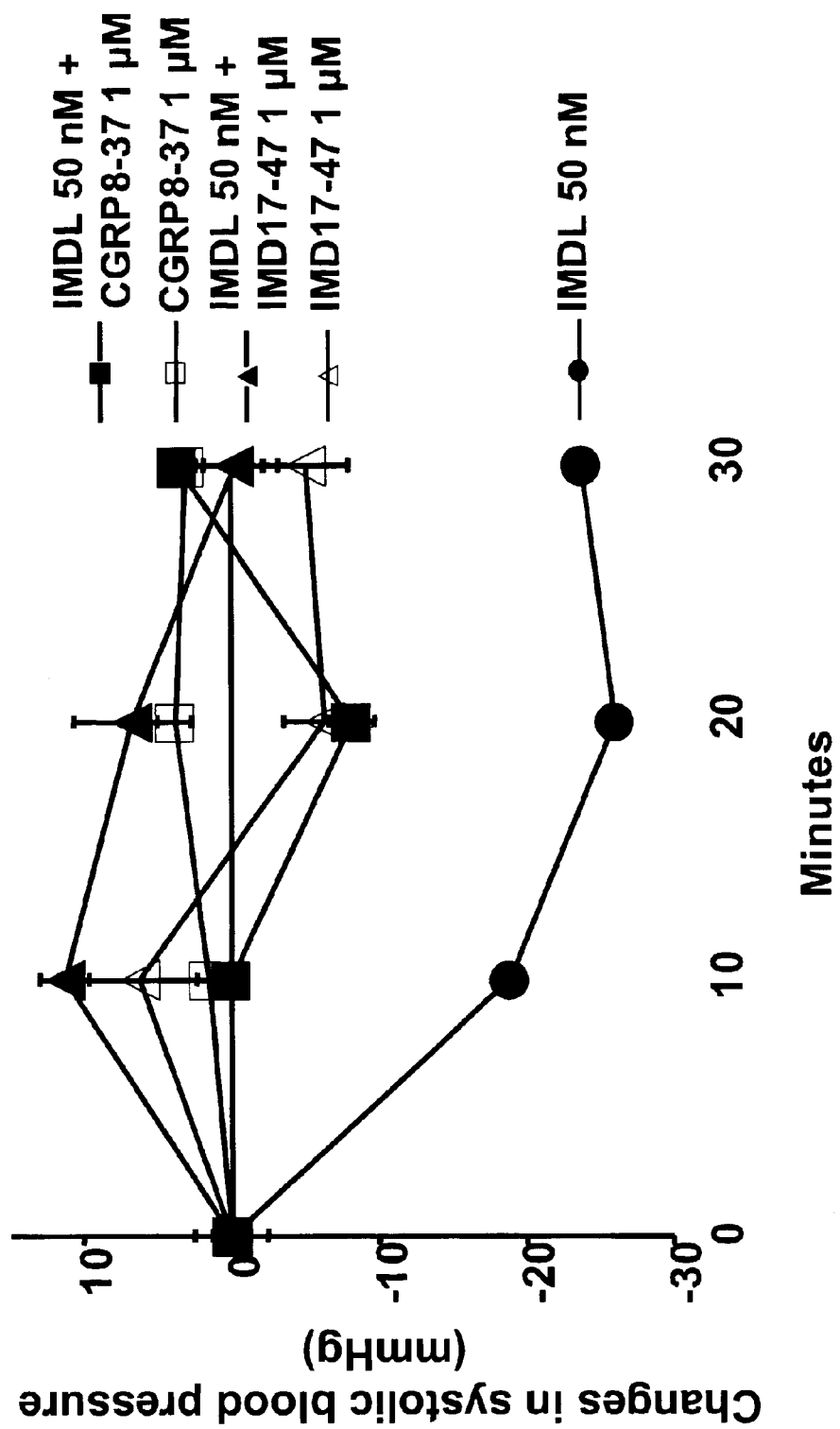
Figure 6D:
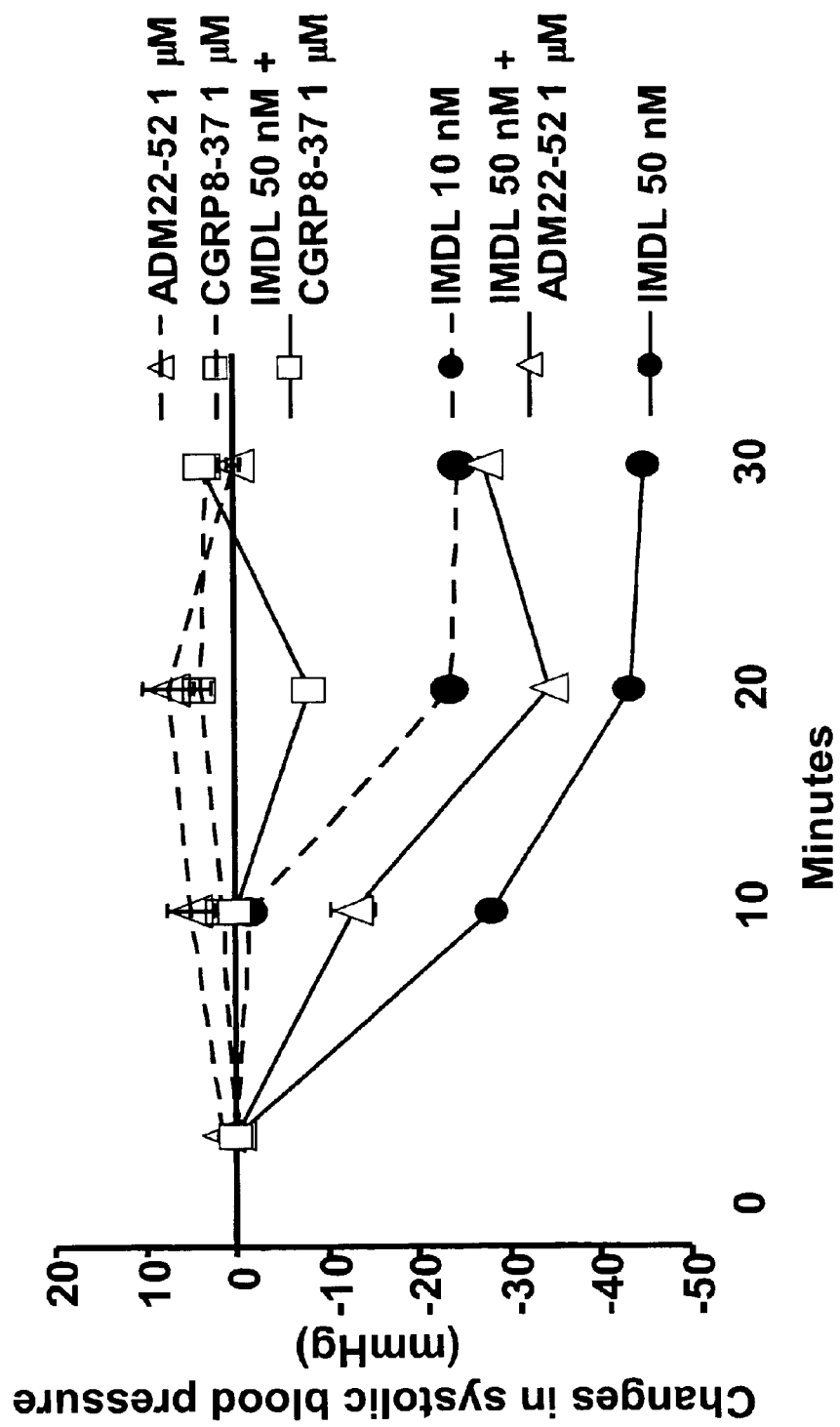

Systemic hypotensive action of intermedin. Because the related ADM is one of the most potent vasodilatators and the pituitary-derived intermedin could be released into systemic circulation to act on diverse peripheral tissues, we tested the effect of intermedin on blood pressure regulation in normal rats and SHR using a noninvasive monitoring approach. As shown in FIG. 6A, intraperitoneal administration of IMDL or IMDS dose-dependently suppressed blood pressure in normal Sprague-Dawley rats, similar to that induced by ADM. In addition, treatment of IMDL or IMDS also increased heart rate as found for ADM (FIG. 6B). In contrast, administration of the truncated IMD17–47 fragment (FIG. 6C) or the prointermedin 55–85 peptide had no effect on blood pressure regulation. Because intermedin signals through CRLR/RAMP receptor complexes, the ability of a CGRP receptor antagonist CGRP8–37 to block the actions of intermedin was also studied. As shown in FIG. 6C, treatment with 20-fold excess CGRP8–37 significantly decreased the hypotensive effects of IMDL. Likewise, cotreatment with the putative intermedin receptor-binding domain fragment IMD17–47 blocked the hypotensive effects of IMDL. In addition, we have studied the hypotensive effect of intermedin in spontaneous hypertensive rats (SHR). Similar to normal rats, IMDL treatment reduced blood pressure in SHR and the hypotensive effects of IMDL were abolished by cotreatment with CGRP8–37 (FIG. 6D). In contrast, cotreatment with the low affinity ADM22–52 fragment had minimal effect. Thus, intermedin is a specific ligand for the vascular CRLR/RAMP signaling system and could be important in the mediation of vascular responses for homeostasis.

Intermedin suppresses food intake and gastric emptying. Earlier studies have shown that both CGRP and ADM have potent anorexic effects and could mediate actions through central or peripheral CRLR/RAMP systems. To examine whether intermedin has a role in anorexia regulation, we studied the ability of intermedin to regulate feeding behavior based on cumulative food intake in fasted mice. Intraperitoneal injection with IMDL, IMDS, ADM, or a type II CRH receptor-selective agonist SRP/urocortin II, decreased food intake in fasted mice (FIG. 7). Because intermedin is specifically expressed in the muscularis mucosae layer of stomach, it could have a role in gastrointestinal functions.

We therefore studied the ability of intermedin to regulate gastric emptying activity in mice. As shown in FIG. 8, intraperitoneal administration of intermedin suppressed gastric emptying activity, similar to the treatment with a known gastric emptying suppression peptide, SRP/urocortin II (15, 23). Likewise, treatment with ADM also suppressed the gastric emptying activity, but with a lower potency. Thus, intermedin could mediate anorexic responses through the regulation of gastrointestinal motility.

In contrast to CGRP and ADM, which exhibit a preferential stimulation of CRLR when coexpressed with RAMP1 and RAMP2 or RAMP3, respectively, intermedin represents a nonselective agonist for the three CRLR/RAMP receptor complexes. Since the discovery of calcitonin in 1960s, the calcitonin/CGRP family peptides have been studied extensively. As a result of gene duplication and functional divergence, this group of peptide hormones acts on diverse systems. Coupled with two closely related GPCRs and three unique RAMPs that transport receptors to the cell surface, a complex ligand-receptor signaling system operates in diverse vertebrates. Calcitonin, CGRP, ADM, and amylin are expressed in a tissue-specific manner with the highest expression in the thyroid C cell, central nervous system, adrenal, and islet B cells, respectively. Although it has been recently established that the signaling by CGRP, ADM, and amylin is unique among peptide hormones and requires the formation of a receptor/RAMP complex, the exact role of these peptides and their cognate receptors in different physiologies remains to be investigated. The present discovery of intermedin as a calcitonin/CGRP family peptide highly expressed in the pituitary and the digestive tract provides a new ligand for peripheral regulation mediated by the CRLR/RAMP system.

As a first step for defining the role of CRLR/RAMP receptor complexes in intermedin signaling, we investigated the activation of CRLR/RAMP receptor complexes in transfected 293T cells, and demonstrated that RAMP is required for mediating intermedin action through CRLR. Of interest, intermedin exhibited a receptor-activation profile distinct from that of CGRP or ADM, suggesting that intermedin could be important for select CRLR/RAMP-mediated physiological processes. It has been shown that the receptor-activation profiles of CGRP and ADM in native tissues are affected by endogenous RAMPs present in different systems.

Among calcitonin/CGRP family peptides, ADM is mainly characterized as a hypotensive hormone whereas CGRP is important for sensory neurotransmission. In addition, ADM inhibits bronchial constriction and acts as a neurohormone to inhibit water drinking and salt appetite. Studies using mutant mice suggested that ADM is indispensable for vascular morphogenesis during embryonic development whereas a CGRP is important for the modulation of sympathetic activity and inflammatory reactions. Therefore, the CRLR in different tissues could mediate the actions of multiple paralogous ligands, and the physiological role of this receptor is partly dependent on activating ligands derived from neighboring cells and/or general circulation.

Because intermedin interacts with CRLR/RAMP receptor complexes, the known receptors for CGRP and ADM, intermedin could regulate diverse physiological functions that have been attributed to ADM or CGRP. As demonstrated in the present study, intermedin decreases blood pressure in both normal rats and SHR as effectively as the better characterized ADM and CGRP, suggesting that intermedin could regulate vasculature homeostasis. Immunohistochemistry studies have shown that CRLR and RAMPs are found in the entire vasculature and the expression of CRLR is mainly in the endothelial layer, therefore, intermedin and related peptides decrease blood pressure via the activation of CRLR/RAMP receptors in the vascular endothelial cells. Concomitant with a hypotensive effect, intermedin treatment also increases heart rate. The increase of heart rate by intermedin and related peptides could be a reflex response to the hypotensive effect. Further, intermedin could have cardioprotective and antibronchial constriction activities that are important for the regulation of cardiac and respiratory homeostasis.

Similar to earlier studies on CGRP and ADM, exogenous intermedin administration was found to exhibit an anorexic effect and suppress stomach emptying responses in mice. These data suggested that intermedin could have roles in the regulation of energy balance via a paracrine mechanism. Because intermedin is expressed in multiple gastrointestinal tissues, intermedin could have additional roles in the gastrointestinal system that remain to be characterized. In support of this view, it has been shown that CRLR is expressed in columnar cells lining the secretory ducts of the parotid gland and in capillaries and venules of the esophagus.

The observation that intermedin is expressed in the anterior and intermediate lobes of the pituitary pointed to a potential role for intermedin and the CRLR/RAMP signaling system in the regulation of pituitary hormone secretion. Although the role of intermedin in the regulation of pituitary hormone secretion has not been examined specifically in the present study, earlier studies on ADM have shown that administration of ADM increases circulating prolactin levels in humans. Therefore, intermedin may play a role in the regulation of pituitary functions. Further studies on the exact expression pattern of intermedin in the pituitary and other tissues during development are important for the understanding of intermedin physiology in pituitary and other tissues.

Earlier studies on the evolution of peptide hormones have shown that selection pressure has favored the conservation of functionally important or mature regions of polypeptide hormone precursors. The finding that only the C-terminal end of the intermedin precursor was conserved during evolution suggested that the C-terminal sequences of the intermedin precursors represent the mature peptide, and further strengthened the theory that sequence conservation among species provides important information on the functional characteristics of gene sequences. Of interest, comparative sequence studies of intermedin precursors from different vertebrates showed that the N-terminal cleavage site of putative mature intermedins vary in position whereas a downstream arginine residue is completely conserved in all species studied. These data indicate that mature intermedin from diverse species could be of varying lengths and a shorter human intermedin (e.g. IMDS) could be generated after posttranslational processing at the downstream basic residue.

Therefore, intermedin is a physiological regulator of gastrointestinal, cardiovascular, and other bioactivities mediated by the CRLR/RAMP receptor complexes. Although the four mammalian CGRP-related peptide hormones, α CGRP, γ CGRP, ADM, and intermedin are capable of interacting with CRLR, optimal regulation by this GPCR signaling pathway likely depends on an integrated release of different endocrine/paracrine ligands in a tissue-specific and time-coordinated manner.

What is claimed is:

1. A composition comprising an isolated and purified intermedin peptide wherein said peptide comprises residues 8–47 of the sequence set forth in SEQ ID NO: 5, wherein said intermedin peptide binds to the calcitonin receptor-like receptor and activates the receptor upon binding.

2. A composition according to claim 1, wherein said peptide comprises residues 1–47 of the sequence set forth in SEQ ID NO: 5.

3. The composition according to claim 1, wherein said composition further comprises a pharmaceutically acceptable carrier.

4. The composition according to claim 1, wherein said peptide comprises the sequence set forth in SEQ ID NO: 2.

* * * * *

SEQUENCE LISTING

<160> NUMBER OF SEQ ID NOS: 5

<210> SEQ ID NO 1
<211> LENGTH: 447
<212> TYPE: DNA
<213> ORGANISM: Homo sapiens
<220> FEATURE:
<221> NAME/KEY: CDS
<222> LOCATION: (1)...(444)

<400> SEQUENCE: 1

```
atg gcc cgg atc ccg acg gcc gcc ctg ggt tgc atc agc ctc ctc tgc      48
Met Ala Arg Ile Pro Thr Ala Ala Leu Gly Cys Ile Ser Leu Leu Cys
 1               5                  10                  15 ctg cag ctc cct ggc tcg ctg tcc cgc agc ctg ggc ggg gac ccg cga      96
Leu Gln Leu Pro Gly Ser Leu Ser Arg Ser Leu Gly Gly Asp Pro Arg
             20                  25                  30 ccc gtc aaa ccc agg gag ccc cca gcc cgg agc cct tcc agc agc ctg     144
Pro Val Lys Pro Arg Glu Pro Pro Ala Arg Ser Pro Ser Ser Ser Leu
         35                  40                  45 cag ccc agg cac ccc gca ccc cga cct gtg gtc tgg aag ctt cac cgg     192
Gln Pro Arg His Pro Ala Pro Arg Pro Val Val Trp Lys Leu His Arg
     50                  55                  60 gcc ctc cag gca cag agg ggt gcc ggc ctg gcc cct gtt atg ggt cag     240
Ala Leu Gln Ala Gln Arg Gly Ala Gly Leu Ala Pro Val Met Gly Gln
 65                  70                  75                  80 cct ctc cgg gat ggt ggc cgc caa cac tcg ggc ccc cga aga cac tcg     288
Pro Leu Arg Asp Gly Gly Arg Gln His Ser Gly Pro Arg Arg His Ser
```

```
                          85                  90                  95
ggc ccc cgc agg acc caa gcc cag ctc ctg cga gtg ggc tgc gtg ctg       336
Gly Pro Arg Arg Thr Gln Ala Gln Leu Leu Arg Val Gly Cys Val Leu
            100                 105                 110 ggc acc tgc cag gtg cag aat ctc agc cac cgc ctg tgg caa ctc atg       384
Gly Thr Cys Gln Val Gln Asn Leu Ser His Arg Leu Trp Gln Leu Met
                115                 120                 125 gga ccg gcc ggc cgg cag gac tca gct cct gtg gac ccc agc agc ccc       432
Gly Pro Ala Gly Arg Gln Asp Ser Ala Pro Val Asp Pro Ser Ser Pro
        130                 135                 140 cac agc tat ggc tga                                                    447
His Ser Tyr Gly
145

<210> SEQ ID NO 2
<211> LENGTH: 148
<212> TYPE: PRT
<213> ORGANISM: Homo sapiens
<220> FEATURE:
<221> NAME/KEY: SIGNAL
<222> LOCATION: (1)...(23)
<220> FEATURE:
<221> NAME/KEY: PEPTIDE
<222> LOCATION: (101)...(147)
<223> OTHER INFORMATION: Mature peptide

<400> SEQUENCE: 2

Met Ala Arg Ile Pro Thr Ala Ala Leu Gly Cys Ile Ser Leu Leu Cys
            -20                 -15                 -10

Leu Gln Leu Pro Gly Ser Leu Ser Arg Ser Leu Gly Gly Asp Pro Arg
        -5                   1                   5

Pro Val Lys Pro Arg Glu Pro Pro Ala Arg Ser Pro Ser Ser Ser Leu
10                  15                  20                  25

Gln Pro Arg His Pro Ala Pro Arg Pro Val Val Trp Lys Leu His Arg
                30                  35                  40

Ala Leu Gln Ala Gln Arg Gly Ala Gly Leu Ala Pro Val Met Gly Gln
            45                  50                  55

Pro Leu Arg Asp Gly Gly Arg Gln His Ser Gly Pro Arg Arg His Ser
        60                  65                  70

Gly Pro Arg Arg Thr Gln Ala Gln Leu Leu Arg Val Gly Cys Val Leu
    75                  80                  85

Gly Thr Cys Gln Val Gln Asn Leu Ser His Arg Leu Trp Gln Leu Met
90                  95                  100                 105

Gly Pro Ala Gly Arg Gln Asp Ser Ala Pro Val Asp Pro Ser Ser Pro
                110                 115                 120

His Ser Tyr Gly
            125

<210> SEQ ID NO 3
<211> LENGTH: 27
<212> TYPE: DNA
<213> ORGANISM: H. sapiens

<400> SEQUENCE: 3
agggagggga actcagcagt tcaggag                                          27

<210> SEQ ID NO 4
<211> LENGTH: 28
<212> TYPE: DNA
<213> ORGANISM: H. sapiens
```

```
<400> SEQUENCE: 4
gttcttgttc ttgctgtcac ttgggcct                                              28

<210> SEQ ID NO 5
<211> LENGTH: 47
<212> TYPE: PRT
<213> ORGANISM: H. sapiens

<400> SEQUENCE: 5

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45
```